US012702584B2

(12) United States Patent
Constant et al.

(10) Patent No.: US 12,702,584 B2
(45) Date of Patent: Aug. 11, 2026

(54) PATIENT CARE SYSTEMS WITH DYNAMIC GATEWAYS

(71) Applicant: Stryker Corporation, Kalamazoo, MI (US)

(72) Inventors: Marco Constant, Portage, MI (US); Madhu Sandeep Thota, Portage, MI (US); Bhavin Kapadia, Portage, MI (US); Krishna Sandeep Bhimavarapu, Kalamazoo, MI (US); Thomas Joseph Durlach, Kalamazoo, MI (US); Frank J. Lee, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 478 days.

(21) Appl. No.: 18/028,301

(22) PCT Filed: Nov. 5, 2021

(86) PCT No.: PCT/US2021/058257

§ 371 (c)(1),
(2) Date: Mar. 24, 2023

(87) PCT Pub. No.: WO2022/099009

PCT Pub. Date: May 12, 2022

(65) Prior Publication Data

US 2023/0363939 A1 Nov. 16, 2023

Related U.S. Application Data

(60) Provisional application No. 63/110,064, filed on Nov. 5, 2020.

(51) Int. Cl.
*A61F 7/00* (2006.01)
*G16H 40/67* (2018.01)

(52) U.S. Cl.
CPC .......... *A61F 7/0085* (2013.01); *G16H 40/67* (2018.01); *A61F 2007/0054* (2013.01); (Continued)

(58) Field of Classification Search
CPC .............................. A61F 7/0085; G16H 40/67
See application file for complete search history.

(56) References Cited

U.S. PATENT DOCUMENTS 10,543,137 B2 1/2020 Hayes et al.
2006/0031991 A1 2/2006 McDaniel et al.
(Continued)

OTHER PUBLICATIONS

PCT International Search Report dated Mar. 7, 2022, for International application No. PCT/US21/58257.

*Primary Examiner* — Kaitlyn E Smith
(74) *Attorney, Agent, or Firm* — Gardner, Linn, Burkhart & Ondersma LLP

(57) ABSTRACT

A medical device, such as a patient support apparatus or a thermal control unit, includes a plurality of mechanical components and a plurality of nodes adapted to communicate with each other over a local network onboard the medical device, and a gateway in communication with an off-board network. The gateway translates messages between the onboard and off-board networks, manages subscriptions to content of the local network, controls bidirectional communication, and otherwise oversees communications between the local and remote networks. The gateway utilizes a configuration file for managing the communications between the off-board and onboard networks, and the gateway is configured to switch to using new or modified configuration files without requiring a reboot or power cycle of the gateway. Updates to the communications between the onboard and off-board networks can therefore be implemented without any downtime and/or without requiring updates to software executables.

16 Claims, 9 Drawing Sheets

(52) U.S. Cl.
CPC ................. *A61F 2007/0056* (2013.01); *A61F 2007/0086* (2013.01); *A61F 2007/0094* (2013.01)

(56) References Cited

U.S. PATENT DOCUMENTS

| | | | |
|---|---|---|---|
| 2011/0087756 | A1 | 4/2011 | Biondi et al. |
| 2012/0182939 | A1 | 7/2012 | Rajan et al. |
| 2013/0150930 | A1 | 6/2013 | Machold et al. |
| 2014/0327751 | A1 * | 11/2014 | King .................. A61B 1/00105 348/75 |
| 2016/0140307 | A1 | 5/2016 | Brosnan et al. |

* cited by examiner

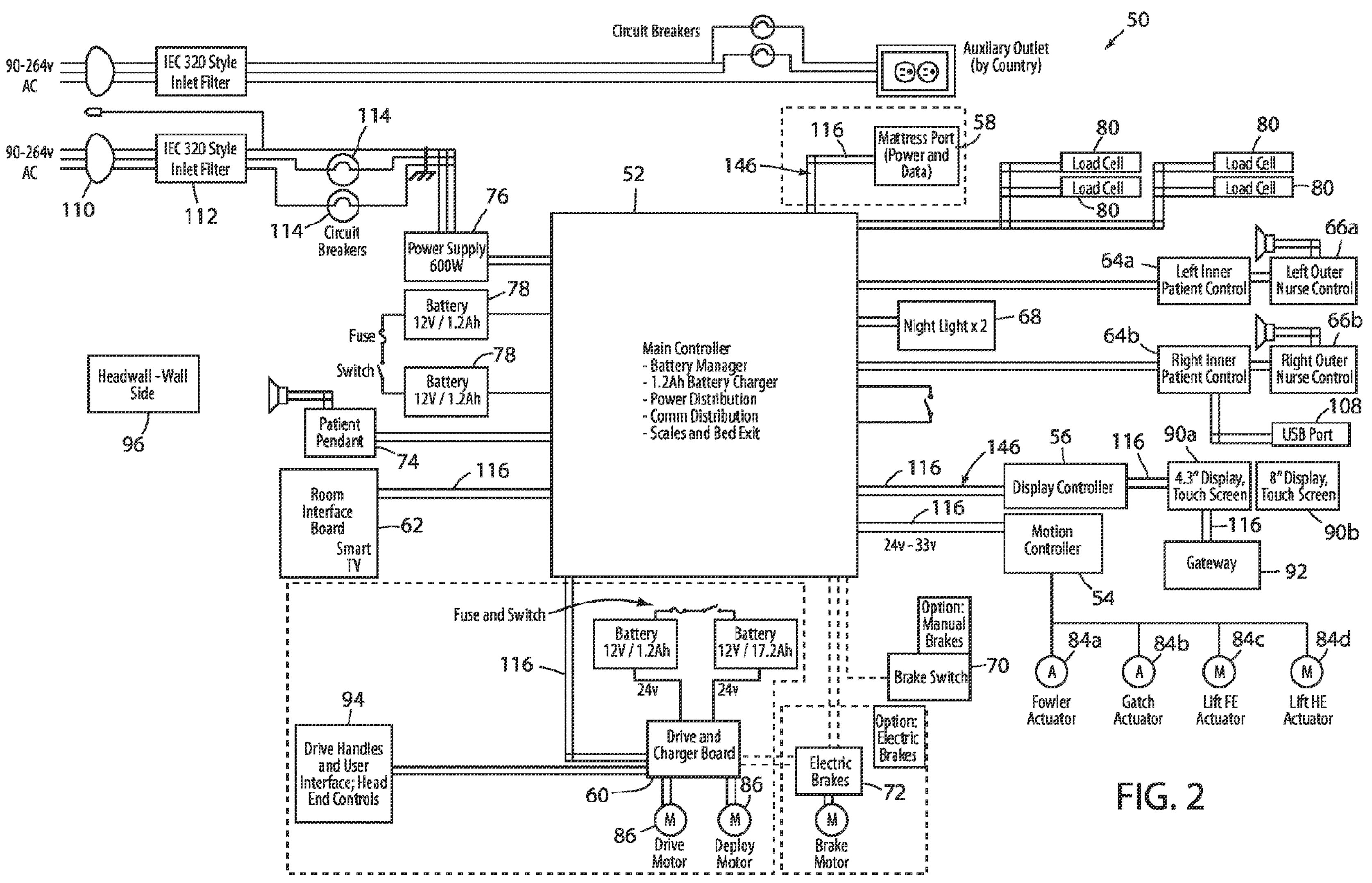
90-264v AC
IEC 320 Style Inlet Filter
Circuit Breakers
Auxilary Outlet (by Country)
50
90-264v AC
110
IEC 320 Style Inlet Filter
112
114
114
Circuit Breakers
76
Power Supply 600W
52
146
116
Mattress Port (Power and Data)
58
80
Load Cell
Load Cell
80
80
Load Cell
Load Cell
80
Battery 12V / 1.2Ah
78
Fuse
Switch
Battery 12V / 1.2Ah
78
Main Controller
- Battery Manager
- 1.2Ah Battery Charger
- Power Distribution
- Comm Distribution
- Scales and Bed Exit
64a
Left Inner Patient Control
Left Outer Nurse Control
66a
Night Light x 2
68
64b
Right Inner Patient Control
Right Outer Nurse Control
66b
108
USB Port
Headwall - Wall Side
96
Patient Pendant
74
116
Room Interface Board
Smart TV
62
116
146
56
Display Controller
116
90a
4.3" Display, Touch Screen
8" Display, Touch Screen
90b
116
116
24v - 33v
Motion Controller
54
Gateway
92
Fuse and Switch
Battery 12V / 1.2Ah
Battery 12V / 17.2Ah
24v
24v
116
Option: Manual Brakes
Brake Switch
70
84a
84b
84c
84d
Fowler Actuator
Gatch Actuator
Lift FE Actuator
Lift HE Actuator
94
Drive Handles and User Interface; Head End Controls
Drive and Charger Board
60
86
86
Drive Motor
Deploy Motor
Option: Electric Brakes
Electric Brakes
72
Brake Motor
FIG. 2

Gateway
Main Controller
I/O Cont-roller
Heat Exchanger Controller
178
178
178

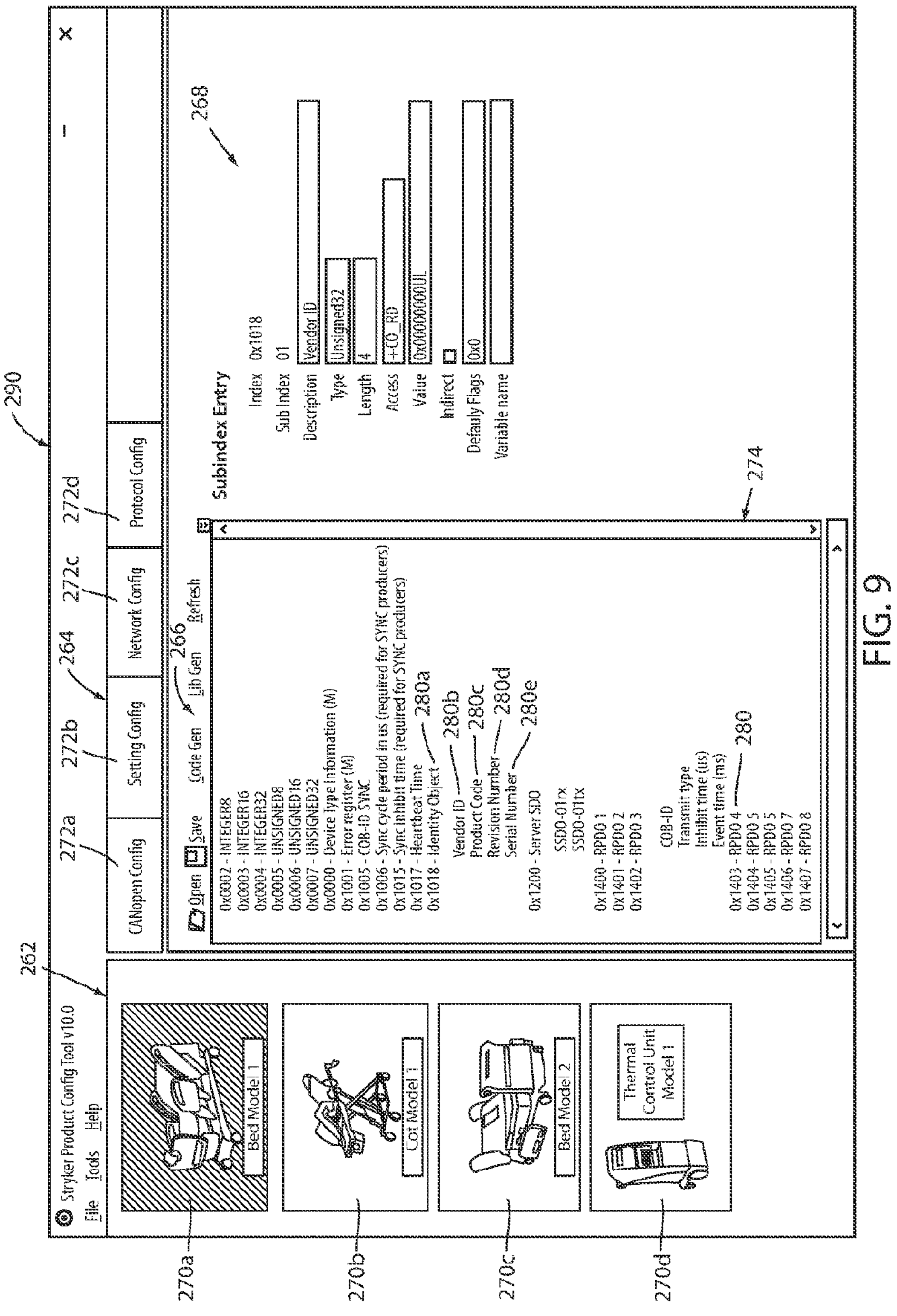

290
262
Stryker Product Config Tool v10.0
File Tools Help
Bed Model 1
Cot Model 1
Bed Model 2
Thermal Control Unit Model 1
270a
270b
270c
270d
272a
272b
264
272c
272d
CANopen Config
Setting Config
Network Config
Protocol Config
Open
Save
Code Gen
Lib Gen
Refresh
266
0x0002 - INTEGER8
0x0003 - INTEGER16
0x0004 - INTEGER32
0x0005 - UNSIGNED8
0x0006 - UNSIGNED16
0x0007 - UNSIGNED32
0x0000 - Device Type Information (M)
0x1001 - Error register (M)
0x1005 - COB-ID SYNC
0x1006 - Sync cycle period in us (required for SYNC producers)
0x1015 - Sync inhibit time (required for SYNC producers)
0x1017 - Heartbeat Time
0x1018 - Identity Object
Vendor ID
Product Code
Revision Number
Serial Number
0x1200 - Server SDO
SSDO-01rx
SSDO-01tx
0x1400 - RPDO 1
0x1401 - RPDO 2
0x1402 - RPDO 3
COB-ID
Transmit type
Inhibit time (us)
Event time (ms)
0x1403 - RPDO 4
0x1404 - RPDO 5
0x1405 - RPDO 5
0x1406 - RPDO 7
0x1407 - RPDO 8
280a
280b
280c
280d
280e
280
274
Subindex Entry
Index 0x1018
Sub Index 01
Description Vendor ID
Type Unsigned32
Length 4
Access +CO_RD
Value 0x00000000UL
Indirect
Defaulty Flags 0x0
Variable name
268
FIG. 9

PATIENT CARE SYSTEMS WITH DYNAMIC GATEWAYS

BACKGROUND

This application claims priority to U.S. provisional patent application Ser. No. 63/110,064 filed Nov. 5, 2020, by inventors Marco Constant et al. and entitled PATIENT CARE SYSTEM WITH DYNAMIC GATEWAY, the complete disclosure of which is incorporated herein by reference.

BACKGROUND

The present disclosure relates to medical devices, such as patient support apparatuses and/or thermal control units, and more particularly to the communications between the patient support apparatus and an off-board computer device, such as a server on a local area network.

Modern day medical devices, such as patient support apparatuses (e.g. beds, cots, stretchers, recliners, chairs, or the like) and/or thermal control units used to control a patient's temperature, often utilize a large number of microcontrollers, actuators, motors, and other electrical components. Groups of these components are often linked together in nodes on the device, and communication between the nodes takes place using various types of embedded network technology, such as, but not limited to, Controller Area Network (CAN) busses, I-squared-C communication, RS-485 links, and/or other types of technology. In some devices of the past, one of the nodes has acted as a gateway node that oversees communication between the local network of nodes onboard the device and an off-board network, such as, but not limited to, a healthcare facility local area network.

SUMMARY

In its various aspects, the present disclosure provides a medical device having a gateway that manages communications between the medical device and one or more devices off-board the medical device. The gateway is configured such that updates, modifications, and/or other changes to the manner in which the medical device communicates with the off-board device(s) can be easily implemented without having to reboot the medical device and/or subject it to a power off/power on cycle. That is, the gateway is controllable such that changes can be implemented in the onboard/-off-board communication while the medical device is operating and without interruption to any of the other functions carried out by the medical device. The gateway implements such changes by reading from a modified configuration file that dictates how the gateway oversees the onboard/off-board communications. Such easily modified communications enable the medical device to change what information it sends to a server (and/or when it sends such information to the server), what information and/or commands it is able to process from the server, and/or what features of the medical device can be managed remotely. The medical device, in some aspects, is a patient support apparatus and/or a thermal control unit.

According to a first aspect of the present disclosure, a patient support apparatus is provided that includes a litter frame, a lift assembly, a support deck, a plurality of node, and a gateway. The lift assembly is adapted to raise and lower the litter frame. The support deck is coupled to the litter frame and adapted to support a patient thereon. The plurality of nodes are adapted to communicate with each other over a local network onboard the patient support apparatus using a first communication protocol. The gateway is in communication with the local network and a remote device. The gateway includes a gateway controller, a first transceiver, a second transceiver, and a memory containing an executable file and a configuration file. The first transceiver is adapted to receive and transmit local messages on the local network that are in a first format, and the second transceiver is adapted to receive and transmit messages on a remote network that are in a second format different from the first format. The executable file contains instructions instructing the gateway controller to perform the following: (a) read the configuration file to identify a set of messages on the local network; (b) monitor the local network for individual messages contained within the set of messages; (c) determine if any of the individual messages contain subscribed content to which a remote device has a subscription; (d) format the subscribed content into outbound messages according to the second format; and (e) forward the outbound messages to the remote network via the second transceiver.

According to a second aspect of the present disclosure, a thermal control unit is provided for controlling a patient's temperature during a thermal therapy session. The thermal control unit includes a circulation channel, a pump, a heat exchanger, a plurality of nodes, a controller, and a gateway. The circulation channel is coupled to a fluid inlet and a fluid outlet. The pump circulates fluid through the circulation channel from the fluid inlet to the fluid outlet. The heat exchanger is adapted to add or remove heat from the fluid circulating in the circulation channel. The plurality of nodes are adapted to communicate with each other over a local network onboard the thermal control unit using a first communications protocol. The controller is adapted to control the heat exchanger in order to control the patient's temperature. The gateway communicates with the local network and a remote device. The gateway includes a gateway controller, a first transceiver, a second transceiver, and a memory containing an executable file and a configuration file. The first transceiver is adapted to receive and transmit local messages on the local network that are in a first format, and the second transceiver is adapted to receive and transmit messages on a remote network that are in a second format different from the first format. The executable file contains instructions instructing the gateway controller to perform the following: (a) read the configuration file to identify a set of messages on the local network; (b) monitor the local network for individual messages contained within the set of messages; (c) determine if any of the individual messages contain subscribed content to which a remote device has a subscription; (d) format the subscribed content into outbound messages according to the second format; and (e) forward the outbound messages to the remote network via the second transceiver.

According to other aspects of the present disclosure, the set of messages on the local network includes a message containing a temperature of the fluid.

In some aspects, the executable file may further contain instructions instructing the gateway controller to read the configuration file to identify the second format.

In some aspects the executable file further contains instructions instructing the gateway controller to perform the following: (i) read the configuration file to identify a set of incoming messages from the remote network; (ii) monitor the second transceiver for individual incoming messages contained within the set of incoming messages; (iii) determine if any of the individual incoming messages contain node content which is to be forwarded to one or more nodes of the local network; (iv) format the node content into local messages according to the first format; and (v) forward the local messages to the local network via the first transceiver.

In some aspects, the executable file further contains instructions instructing the gateway controller to perform the following: (i) receive a new configuration file; (ii) replace the configuration file with the new configuration file; and (iii) perform steps (a) through (e) using the new configuration file. The gateway controller may further be adapted to perform steps (i) through (iii) without being rebooted and without installing a different executable file. Still further, in some aspects, the executable file contains instructions instructing the gateway controller to receive the new configuration file via the second transceiver.

In some aspects, the patient support apparatus or thermal control unit includes a third transceiver and the executable file contains instructions instructing the gateway controller to receive the new configuration file via the third transceiver.

The executable file, in some aspects, further contains instructions instructing the gateway controller to read the configuration file to determine an address of the remote device.

In some aspects, the patient support apparatus or thermal control unit further comprises a third transceiver in communication with the gateway controller and the remote network. The third transceiver is adapted transmit and receive messages on the remote network that are in a third format, and the executable file contains instructions instructing the gateway controller to perform the following: (i) receive a new configuration file; (ii) replace the configuration file with the new configuration file; (iii) read the new configuration file to identify a new set of messages on the local network; (iv) monitor the local network for individual messages contained within the new set of messages; (v) determine if any of the individual messages contained within the new set of message contain subscribed content to which the remote device has a subscription; (vi) read the new configuration file to determine which of the second transceiver and third transceivers is a selected transceiver for communicating the subscribed content to the remote device; (vii) format the subscribed content into outbound messages according to a corresponding format of the selected transceiver; and (viii) forward the outbound messages to the remote network via the selected transceiver.

In some aspects, the first format is a Controller Area Network (CAN) message format and the second format is a JavaScript Object Notation format.

The configuration file, in some aspects, is an eXtensible Markup Language (XML) file.

The second format, in some aspects, is an XML information set adapted to be used with a Simple Object Access Protocol (SOAP) between the second transceiver and the remote network.

The configuration file, in some aspects, includes at least two of the following: a Service Set Identifier (SSID) for the remote network, a password for accessing the remote network, a Transmission Control Protocol (TCP) port number for communicating with the remote device, an IP address of the remote device, a definition of the first format, or a definition of the second format.

According to another aspect of the present disclosure, a patient support apparatus is provided that includes a frame, a lift assembly, a support deck, a plurality of node, and a gateway. The lift assembly is adapted to raise and lower the litter frame. The support deck is coupled to the litter frame and adapted to support a patient thereon. The plurality of nodes are adapted to communicate with each other over a local network onboard the patient support apparatus using a first communication protocol. The gateway is in communication with the local network and a remote device. The gateway includes a gateway controller, a first transceiver, a second transceiver, and a memory containing an executable file and a configuration file. The first transceiver is adapted to receive and transmit local messages on the local network that are in a first format, and the second transceiver is adapted to receive and transmit messages on a remote network that are in a second format different from the first format. The executable file contains instructions instructing the gateway controller to perform the following: (a) read the configuration file to identify a set of messages to be received from the remote network; (b) monitor the second transceiver for individual messages contained within the set of messages; (c) read the configuration file to determine if any of the individual messages contain node content to be forwarded to an individual node of the plurality of nodes on the local network; (d) format the node content into onboard messages according to the first format; and (e) forward the onboard messages to the local network via the first transceiver.

According to yet another aspect of the present disclosure, a thermal control unit is provided for controlling a patient's temperature during a thermal therapy session. The thermal control unit includes a circulation channel, a pump, a heat exchanger, a plurality of nodes, a controller, and a gateway. The circulation channel is coupled to a fluid inlet and a fluid outlet. The pump circulates fluid through the circulation channel from the fluid inlet to the fluid outlet. The heat exchanger is adapted to add or remove heat from the fluid circulating in the circulation channel. The plurality of nodes are adapted to communicate with each other over a local network onboard the thermal control unit using a first communications protocol. The controller is adapted to control the heat exchanger in order to control the patient's temperature. The gateway communicates with the local network and a remote device. The gateway includes a gateway controller, a first transceiver, a second transceiver, and a memory containing an executable file and a configuration file. The first transceiver is adapted to receive and transmit local messages on the local network that are in a first format, and the second transceiver is adapted to receive and transmit messages on a remote network that are in a second format different from the first format. The executable file contains instructions instructing the gateway controller to perform the following: (a) read the configuration file to identify a set of messages to be received from the remote network; (b) monitor the second transceiver for individual messages contained within the set of messages; (c) read the configuration file to determine if any of the individual messages contain node content to be forwarded to an individual node of the plurality of nodes on the local network; (d) format the node content into onboard messages according to the first format; and (e) forward the onboard messages to the local network via the first transceiver.

According to another aspect of the present disclosure, the set of messages from the remote network includes a message requesting a reading of a current temperature of the fluid.

In some aspects, the executable file may further contain instructions instructing the gateway controller to read the configuration file to identify the first format.

The executable file, in some aspects, includes instructions instructing the gateway controller to perform the following: (i) read the configuration file to identify a set of local messages on the local network; (ii) monitor the local network for individual local messages contained within the set of local messages; (iii) determine if any of the individual local messages contain subscribed content to which a remote device has a subscription; (iv) format the subscribed content into outbound messages according to the second format; and (v) forward the outbound messages to the remote network via the second transceiver.

In some aspects, the executable file further contains instructions instructing the gateway controller to read the configuration file to determine an address of the remote device.

In some aspects, the patient support apparatus or thermal control unit further includes a third transceiver in communication with the gateway controller and the remote network. The third transceiver is adapted to transmit and receive messages on the remote network that are in a third format, and the executable file contains instructions instructing the gateway controller to perform the following: (i) receive a new configuration file; (ii) replace the configuration file with the new configuration file; (iii) read the new configuration file to identify a new set of messages receivable from the remote network; (iv) monitor the second transceiver for new individual messages contained within the new set of messages; (v) read the new configuration file to determine if any of the new individual messages contain new node content to be forwarded to an individual node of the plurality of nodes on the local network; (vi) format the new node content into new onboard messages according to the first format; and (vii) forward the new onboard messages to the local network via the first transceiver.

According to another aspect of the present disclosure, a patient support apparatus is provided that includes a litter frame.

According to another aspect of the present disclosure, a patient support apparatus is provided that includes a litter frame, a lift assembly, a support deck, a plurality of nodes, and a gateway. The lift assembly is adapted to raise and lower the litter frame. The support deck is coupled to the litter frame and adapted to support a patient thereon. The plurality of nodes are adapted to communicate with each other over a local network onboard the patient support apparatus using a first communication protocol. The gateway is in communication with the local network and a remote device. The gateway includes a gateway controller, a first transceiver, a second transceiver, and a memory containing an executable file and a configuration file. The first transceiver is adapted to receive and transmit local messages on the local network that are in a first format, and the second transceiver is adapted to receive and transmit messages on a remote network that are in a second format different from the first format. The executable file contains instructions instructing the gateway controller to perform the following: (a) read the configuration file to identify a first set of messages on the local network; (b) forward content from the first set of messages to the remote device in the second format; (c) receive a new configuration file and, without rebooting the gateway controller, perform the following: (i) read the new configuration file to identify a second set of messages on the local network; (ii) read the new configuration file to identify a device address associated with the second set of messages and a particular message format associated with the device address; and (iii) forward content from the second set of messages to the device address using the particular message format.

According to yet another aspect of the present disclosure, a thermal control unit is provided for controlling a patient's temperature during a thermal therapy session. The thermal control unit includes a circulation channel, a pump, a heat exchanger, a plurality of nodes, a controller, and a gateway. The circulation channel is coupled to a fluid inlet and a fluid outlet. The pump circulates fluid through the circulation channel from the fluid inlet to the fluid outlet. The heat exchanger is adapted to add or remove heat from the fluid circulating in the circulation channel. The plurality of nodes are adapted to communicate with each other over a local network onboard the thermal control unit using a first communications protocol. The controller is adapted to control the heat exchanger in order to control the patient's temperature. The gateway communicates with the local network and a remote device. The gateway includes a gateway controller, a first transceiver, a second transceiver, and a memory containing an executable file and a configuration file. The first transceiver is adapted to receive and transmit local messages on the local network that are in a first format, and the second transceiver is adapted to receive and transmit messages on a remote network that are in a second format different from the first format. The executable file contains instructions instructing the gateway controller to perform the following: (a) read the configuration file to identify a first set of messages on the local network; (b) forward content from the first set of messages to the remote device in the second format; (c) receive a new configuration file and, without rebooting the gateway controller, perform the following: (i) read the new configuration file to identify a second set of messages on the local network; (ii) read the new configuration file to identify a device address associated with the second set of messages and a particular message format associated with the device address; and (iii) forward content from the second set of messages to the device address using the particular message format.

According to another aspect of the present disclosure, the first set of messages on the local network includes a first message containing a temperature of the fluid in the thermal control unit but does not include a second message indicating a flow rate of the fluid through the circulation channel, and the second set of messages includes the second message.

In some aspects, the device address may be the same as, or different from, an address associated with the remote device.

In some aspects, the particular message format is the same as the second format, while in other aspects, the particular message format is different from the second format.

In some aspects, the executable file further contains instructions instructing the gateway controller to perform the following: (i) read the configuration file to identify a set of incoming messages from the remote network; (ii) monitor the second transceiver for individual incoming messages contained within the set of incoming messages; (iii) determine if any of the individual incoming messages contain node content which is to be forwarded to one or more nodes of the local network; (iv) format the node content into local messages according to the first format; and (v) forward the local messages to the local network via the first transceiver.

In some aspects, the executable file contains instructions instructing the gateway controller to receive the new configuration file via the second transceiver.

In some aspects, the second set of messages includes a new message not contained within the first set of messages, and the new message contains data from a sensor in communication with a particular node of the plurality of nodes.

According to another aspect of the present disclosure, a patient support apparatus is provided that includes a litter frame, a lift assembly, a support deck, a plurality of node, and a gateway. The lift assembly is adapted to raise and lower the litter frame. The support deck is coupled to the litter frame and adapted to support a patient thereon. The plurality of nodes are adapted to communicate with each other over a local network onboard the patient support apparatus using a first communication protocol. The gateway is in communication with the local network and a remote device. The gateway includes a gateway controller, a first transceiver, a second transceiver, and a memory containing an executable file and a configuration file. The first transceiver is adapted to receive and transmit local messages on the local network that are in a first format, and the second transceiver is adapted to receive and transmit messages on a remote network that are in a second format different from the first format. The executable file contains instructions instructing the gateway controller to perform the following: (a) read the configuration file to identify a first set of messages to be received from the remote network and forwarded to the local network; (b) forward content from the first set of messages to the local network in the first format; (c) receive a new configuration file and, without rebooting the gateway controller, perform the following: (i) read the new configuration file to identify a second set of messages to be received from the remote network and forwarded to the local network; and (ii) forward content from the second set of messages to the local network.

According to yet another aspect of the present disclosure, a thermal control unit is provided for controlling a patient's temperature during a thermal therapy session. The thermal control unit includes a circulation channel, a pump, a heat exchanger, a plurality of nodes, a controller, and a gateway. The circulation channel is coupled to a fluid inlet and a fluid outlet. The pump circulates fluid through the circulation channel from the fluid inlet to the fluid outlet. The heat exchanger is adapted to add or remove heat from the fluid circulating in the circulation channel. The plurality of nodes are adapted to communicate with each other over a local network onboard the thermal control unit using a first communications protocol. The controller is adapted to control the heat exchanger in order to control the patient's temperature. The gateway communicates with the local network and a remote device. The gateway includes a gateway controller, a first transceiver, a second transceiver, and a memory containing an executable file and a configuration file. The first transceiver is adapted to receive and transmit local messages on the local network that are in a first format, and the second transceiver is adapted to receive and transmit messages on a remote network that are in a second format different from the first format. The executable file contains instructions instructing the gateway controller to perform the following: (a) read the configuration file to identify a first set of messages to be received from the remote network and forwarded to the local network; (b) forward content from the first set of messages to the local network in the first format; (c) receive a new configuration file and, without rebooting the gateway controller, perform the following: (i) read the new configuration file to identify a second set of messages to be received from the remote network and forwarded to the local network; and (ii) forward content from the second set of messages to the local network.

According to another aspect of the present disclosure, the first set of messages from the remote network includes a first message requesting a reading of a current temperature of the fluid in the thermal control unit but does not include a second message requesting a reading of a current flow rate of the fluid through the circulation channel, and the second set of messages includes the second message.

According to other aspects, the executable file may further contain instructions instructing the gateway controller to read the configuration file to identify the first format.

In some aspects, the executable file further contains instructions instructing the gateway controller to perform the following: (i) read the new configuration file to identify a set of local messages on the local network; (ii) monitor the local network for individual local messages contained within the set of local messages; (iii) determine if any of the individual local messages contain subscribed content to which the remote device has a subscription; (iv) format the subscribed content into outbound messages according to the second format; and (v) forward the outbound messages to the remote network via the second transceiver.

In some aspects, the second set of messages includes a new message not contained within the first set of messages, and the new message instructs a particular node on the patient support apparatus or thermal control unit to activate a sensor in communication with the particular node and to report a reading from the sensor to the local network.

In some aspects, the executable file further contains instructions instructing the gateway controller to read the new configuration file to identify a message ID associated with the second set of messages, and to attach the message ID to the content forwarded from the second set of messages to the local network.

According to still another aspect of the present disclosure, a gateway configuration tool is provided for generating a configuration file for use in a gateway node of at least one of a patient support apparatus or a thermal control unit. The gateway configuration tool includes a non-transitory computer readable medium with computer executable instructions stored thereon adapted to be executed by a processor of a computer having a display. The computer executable instructions are adapted to cause, when executed, the processor to perform the following: (i) display a selection option on the display for selecting at least one of a model of a patient support apparatus or a model of a thermal control unit; (ii) display an onboard message editing area in which a user is able to define characteristics of a first set of messages that travel over an onboard network positioned onboard the selected model and that are to be transmitted to an off-board device by the gateway node of the selected model; (iii) display an off-board message editing area in which a user is able to define characteristics of a second set of messages that are receivable by the gateway node from the off-board device and that are to be delivered onto the onboard network by the gateway node; and (iv) generate a configuration file using the first and second sets of messages. The configuration file is adapted to be used by the gateway node without requiring the gateway node to be re-booted or power cycled.

According to other aspects of the present disclosure, the non-transitory computer readable medium may further be adapted to cause the processor, when executed, to perform the following: define a first protocol to be used by the gateway node when transmitting the first set of messages to the off-board device; and define a second protocol to be used by the gateway node when delivering the second set of messages to the onboard network.

According to some aspects, the configuration file is an eXtensible Markup Language (.xml) file.

In some aspects, the onboard message editing area of the gateway configuration tool includes a Controller Area Network (CAN) option that, when selected, causes the processor to perform the following: display a CAN message editing area in which the user is able to define characteristics of CAN messages. The CAN messages are included within the first set of messages.

In some aspects, the non-transitory computer readable medium is further adapted to cause the processor, when executed, to perform the following: display a plurality of options for editing a plurality of different types of data for the configuration file.

The plurality of options, in some aspects, includes a settings option, a network configurations option, and a protocol configuration option.

In some aspects, the plurality of options includes at least one of the following: a transceiver option, a command option, an addresses option, a retrievable data option, a subscription option, or a formatting option.

In some aspects, wherein the selected model is the model of the thermal therapy unit, the configuration file may be adapted to cause the gateway node of the thermal therapy unit to perform the following: (i) monitor the onboard network for a first message containing a current temperature of the fluid; (ii) convert the first message to a second message formatted according to the second protocol; and (iii) transmit the second message to the off-board device.

In some aspects, wherein the selected model is the model of the patient support apparatus, the configuration file may be adapted to cause the gateway node of the patient support apparatus to perform the following: (i) monitor the onboard network for a first message containing a current status of a brake onboard the patient support apparatus; (ii) convert the first message to a second message formatted according to the second protocol; and (iii) transmit the second message to the off-board device.

Before the various aspects disclosed herein are explained in detail, it is to be understood that the claims are not to be limited to the details of operation, to the details of construction, or to the arrangement of the components set forth in the following description or illustrated in the drawings. The aspects described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various aspects. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 2 is a diagram of a control system that may be used with the patient support apparatus of FIG. 1;

FIG. 9 is a second illustrative screenshot of the configuration tool of FIG. 8 showing a portion of an object dictionary that may be edited using the tool.

DETAILED DESCRIPTION OF THE DISCLOSURE

Figure 1:
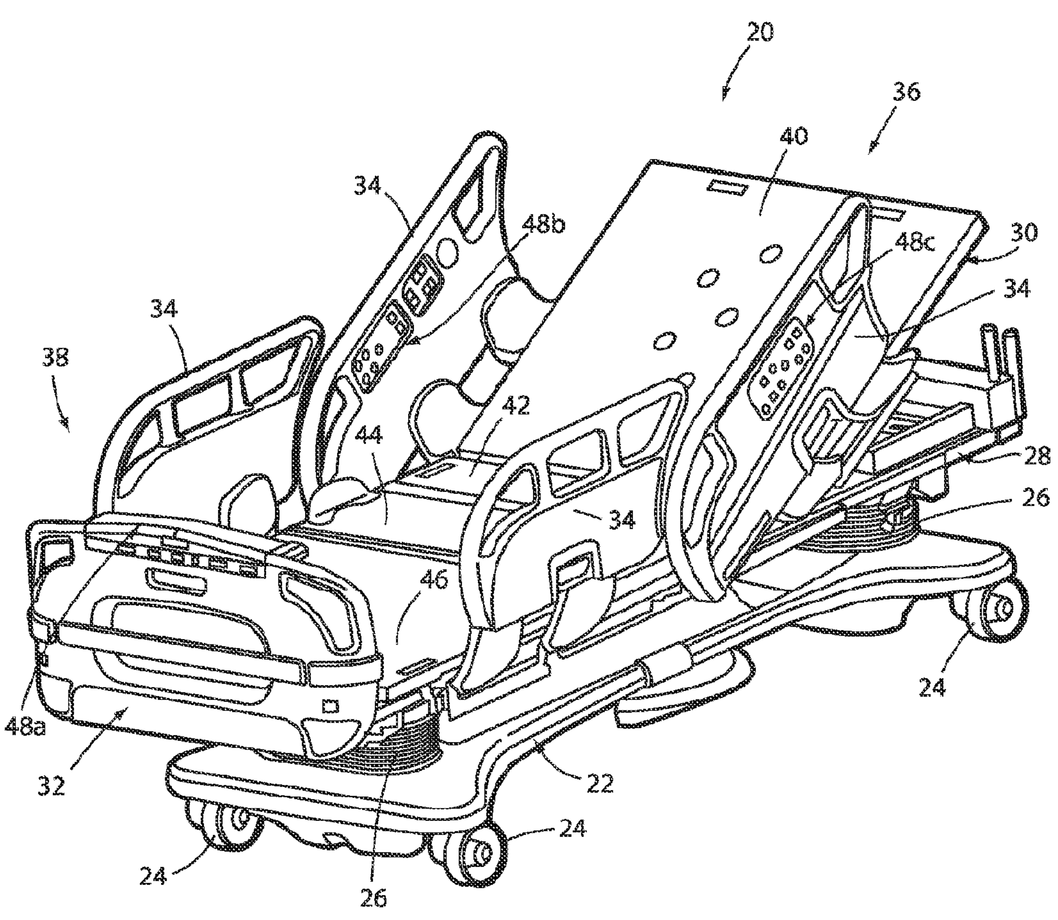
FIG. 1 is perspective view of a patient support apparatus into which one or more of the features of the present disclosure may be incorporated.

A patient support apparatus 20 according to one embodiment of the present disclosure is shown in FIG. 1. Although the particular form of patient support apparatus 20 illustrated in FIG. 1 is a bed adapted for use in a hospital or other medical setting, it will be understood that the patient support apparatus 20 could, in different embodiments, be a cot, a stretcher, a gurney, a recliner, or any other structure capable of supporting a patient that may be used during times when the patient is not accompanied by a caregiver. For purposes of the following written description, the patient support apparatus 20 will be described as a bed with the understanding the following written description applies to these other types of patient support apparatuses.

In general, the patient support apparatus 20 includes a base 22 having a plurality of wheels 24, a lift subsystem comprising a pair of lifts 26 supported on the base, a litter frame 28 supported on the lifts 26, and a support deck 30 supported on the litter frame 28. Patient support apparatus 20 further includes a headboard (not shown), a footboard 32, and a plurality of siderails 34. Siderails 34 are all shown in a raised position in FIG. 1 but are each individually movable to a lower position in which ingress into, and egress out of, patient support apparatus 20 is not obstructed by the lowered siderails 34. In some embodiments, the siderails 34 may be moved to one or more intermediate positions as well.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 36 and a foot end 38, each of whose height can be independently adjusted by the nearest lift 26. The patient support apparatus 20 is designed so that when an occupant lies thereon, his or her head will be positioned adjacent head end 36 and his or her feet will be positioned adjacent foot end 38.

Litter frame 28 provides a structure for supporting support deck 30, the headboard, footboard 32, and siderails 34. Support deck 30 provides a support surface for a mattress (not shown in FIG. 1), or other soft cushion, so that a person may lie and/or sit thereon. The support deck 30 is made of a plurality of sections, some of which are pivotable about generally horizontal pivot axes. In the embodiment shown in FIG. 1, the support deck 30 includes a head section 40, a seat section 42, a thigh section 44, and a foot section 46. Head section 40, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 44 and foot section 46 may also be pivotable about generally horizontal pivot axes.

Patient support apparatus 20 further includes a plurality of user interfaces or control panels 48 that enable a user of patient support apparatus 20, such as a patient and/or an associated caregiver, to control one or more aspects of patient support apparatus 20. In the embodiment shown in FIG. 1, patient support apparatus 20 includes a footboard control panel 48*a*, a pair of inner siderail patient control panels 48*b* (only one of which is visible), and a pair of outer siderail caregiver control panels 48*c* (only one of which is visible). Footboard control panel 48*a* and outer siderail control panels 48*c* are intended to be used by caregivers, or other authorized personnel, while inner siderail control panels 48*b* are intended to be used by the patient associated with patient support apparatus 20.

Figure 3:
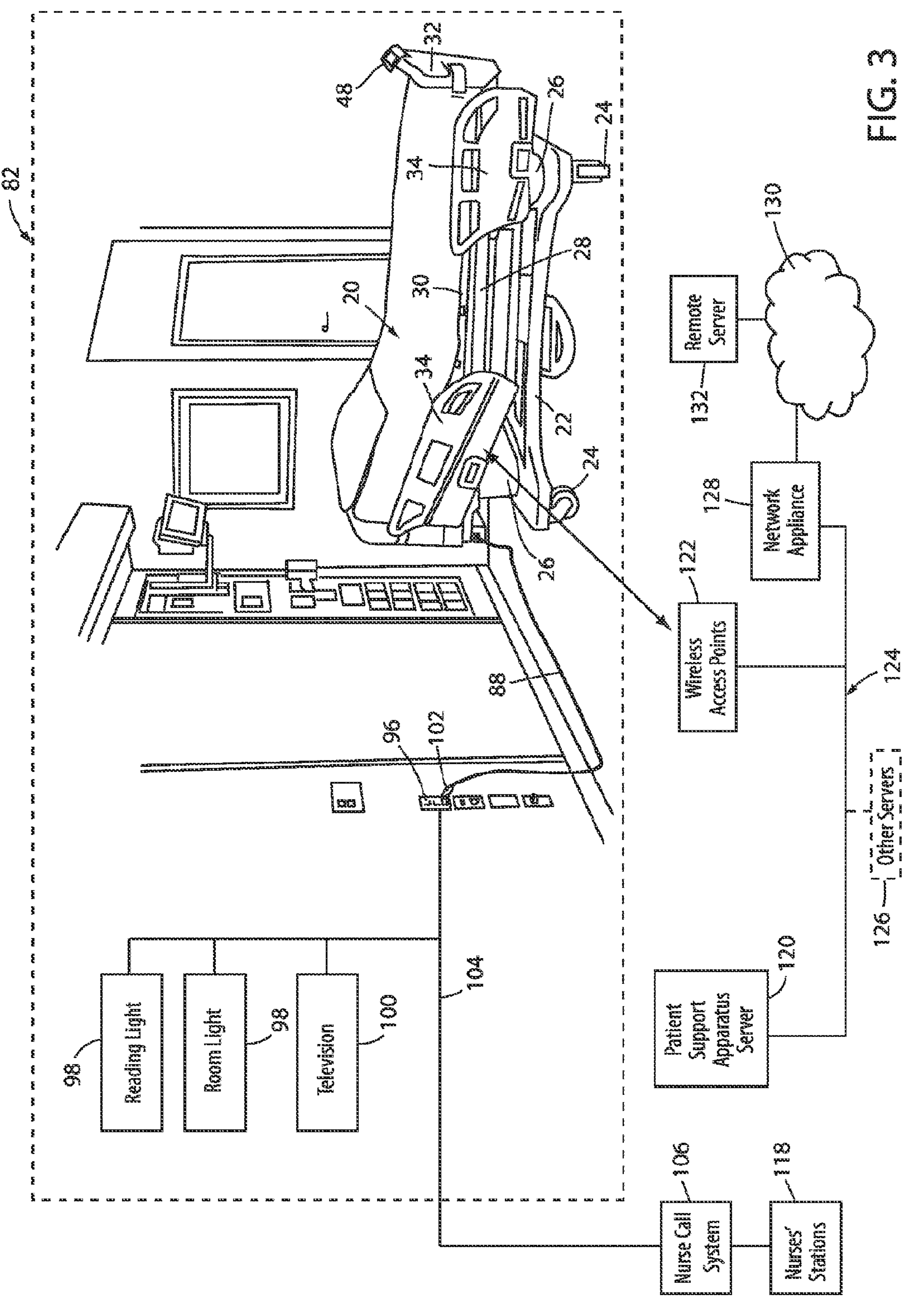
FIG. 3 is a perspective view of the patient support apparatus of FIG. 1 shown in an illustrative healthcare facility and communicatively coupled to an illustrative local area network of the healthcare facility.

Not all of the control panels 48 include the same controls and/or functionality. In the illustrated embodiment, footboard control panel 48*a* includes a substantially complete set of controls for controlling patient support apparatus 20 while control panels 48*b* and 48*c* include a selected subset of those controls (and/or other controls). Control panels 48 may include controls for allowing a user to do one or more of the following: change a height of support deck 30, raise or lower head section 40, activate and deactivate a brake for wheels 24, arm an exit detection system, take a weight reading of the patient, activate and deactivate a propulsion system, and communicate with a healthcare facility computer network installed in the healthcare facility in which patient support apparatus 20 is positioned. Inner siderail control panels 48*b* may also include a nurse call control that enables a patient to call a nurse. A speaker and microphone are included in order to allow the patient to orally communicate with the remotely positioned nurse, such as, but not limited to, a nurse positioned at a remote nurses station 118 (FIG. 3).

The controls for carrying out any of the aforementioned functions may be implemented as buttons, dials, switches, or other devices. Any of control panels 48*a-c* may also include a display for displaying information regarding patient support apparatus 20. The display is a touchscreen in some embodiments, and may include one or more control icons for carrying out any of the control functions described herein.

The mechanical construction of those aspects of patient support apparatus 20 not explicitly described herein may be the same as, or nearly the same as, the mechanical construction of the Model 3002 S3® bed manufactured and sold by Stryker Corporation of Kalamazoo, Michigan. This mechanical construction is described in greater detail in the Stryker Maintenance Manual for the S3® MedSurg Bed, Model 3002, published in 2018 (document 3006.609.002 Rev E) by Stryker Corporation of Kalamazoo, Michigan, the complete disclosure of which is incorporated herein by reference. It will be understood by those skilled in the art that those aspects of patient support apparatus 20 not explicitly described herein can alternatively be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. As yet another alternative, the mechanical construction of patient support apparatus 20 can take on the form of any or all of the Model 5900 MV3® bariatric bed manufactured and sold by Stryker Corporation of Kalamazoo, MI, the details of which are described in the Stryker Maintenance Manual for the MV3® Bariatric Bed (Ref. 5900), published in 2020 (document 5900.009.002 Rev. C.1) by Stryker Corporation, the complete disclosure of which is incorporated herein by reference. The mechanical construction of patient support apparatus 20 may also take on forms different from what is disclosed in the aforementioned references.

Referring now to FIG. 2, patient support apparatus 20 includes a control system 50 that controls the various electrical and mechanical functions of patient support apparatus 20. Control system 50 includes a main control node 52 electrically coupled to a plurality of other control boards, including a motion control node 54, a display control node 56, a mattress control node 58, a propulsion control node 60, a room interface node 62, a left inner siderail control panel board 64*a*, a right inner siderail control panel board 64*b*, a left outer siderail control panel board 66*a*, and a right outer siderail control panel board 66*b*. All of the aforementioned nodes and circuit boards communicate with main control node 52 over one or more internal network communication buses and/or protocols, such as, but not limited to, one or more Controller Area Network (CAN) buses that operate in accordance with one or more of the ISO standards 11898-1, 11898-2, and/or 11898-3. Alternatively, or additionally, two or more nodes or circuit boards of control system 50 may communicate using the CAN FD 1.0 (Flexible Data-Rate) standard. Still further, some of the boards and/or nodes of control system 50 may alternatively or additionally communicate using the Local Interconnect Network (LIN) serial network protocol, the RS-485 serial protocol, the I-Squared-C serial communication bus, and/or the Ethernet protocol. Indeed, in some embodiments, two or more of the boards and/or nodes of control system 50 may translate messages from one protocol to another, such as is disclosed in commonly assigned U.S. patent application Ser. No. 15/903,477 filed Feb. 23, 2018, by inventors Krishna Bhimavarapu et al. and entitled PATIENT CARE DEVICES WITH ON-BOARD NETWORK COMMUNICATION, the complete disclosure of which is hereby incorporated herein by reference.

In addition to the aforementioned nodes and boards, main control node 52 of control system 50 is also adapted to communicate with the following: a night light 68, a brake switch 70, an electric brake 72, a patient pendant 74, and a power supply 76. Main control node 52 receives electrical power from power supply 76 and/or a pair of main batteries 78. Still further, main control node 52 is in communication with four load cells 80 that are part of a scale/exit detection system.

All of the nodes 52-62, 92 include at least one microcontroller that oversees the operation of the functions carried out by that node. Thus, for example, main node 52 includes a main microcontroller that oversees the general operation of patient support apparatus 20. This main microcontroller oversees the distribution of electrical power to the various components of patient support apparatus 20. Motion control node 54 similarly includes a motion microcontroller that controls the movement of those components of patient support apparatus 20 that are able to be moved on patient support apparatus 20. In the embodiment shown in FIG. 2, motion control node 54 communicates with, and controls the operation of, four motorized actuators 84. These include a Fowler actuator 84*a*, a gatch actuator 84*b*, a foot end lift actuator 84*c*, and a head end lift actuator 84*d*. Fowler actuator 84*a* pivots of head section (also known as a Fowler section) 40 of support deck 30 about a generally horizontal pivot axis. Gatch actuator 84*b* raises and lowers the joint between thigh section 44 and foot section 46 of support deck 30. Gatch actuator 84*b* therefore raises and lowers the patient's knees when the patient is lying on a mattress positioned on top of support deck 30. Foot end lift actuator 84*c* moves the lift 26 positioned toward foot end 38 of patient support apparatus 20 upward and downward. Head end lift actuator 84*d* moves the lift positioned toward head end 36 of patient support apparatus 20 upward and downward.

Motorized actuators 84 of control system 50 may be linear actuators, rotary actuators, or other types of actuators capable of raising, lowering, and/or pivoting the components of patient support apparatus 20 to which they are coupled. Actuators 84 are electrically powered in the illustrated embodiments, but may alternatively be implemented as hydraulic, electro-hydraulic, pneumatic, or the like. Actuators 84 are controlled in response to the activation of one or more controls positioned on one or more of the control panels 48*a*-48*c*. In some embodiments, one or more of the actuators 84 are implemented in any of the manners disclosed in commonly assigned U.S. patent application Ser. No. 15/449,277 filed Mar. 3, 2017 by inventors Aaron Furman et al. and entitled PATIENT SUPPORT APPARATUS WITH ACTUATOR FEEDBACK, the complete disclosure of which is incorporated herein by reference. Other types of actuators may of course be used.

Motion control node 54 (FIG. 2) controls the movement of the motors within actuators 84 by sending a pulse width modulated (PWM) signal to the motors in response to a user activating one of the actuator controls on one or more of the control panels 48. By changing the duty cycle of the PWM signals sent to the motor, motion control node 54 is able to control the speed of the motor. In some embodiments, motion control node 54 controls the operation of each motor of each actuator 84 using an H-bridge of the type disclosed in commonly assigned U.S. patent application Ser. No. 14/838,693 filed Aug. 28, 2015, by inventors Daniel Brosnan et al. and entitled PERSON SUPPORT APPARATUS WITH ACTUATOR BRAKE CONTROL, the complete disclosure of which is incorporated herein by reference. Motion control node 54 may utilize the braking technique disclosed in the aforementioned '693 application, or it may use another braking technique. Still further, motion control node 54 may control the motors of actuators 84 in manners other than using PWM signals and/or in other manners than what is disclosed in the aforementioned '693 application.

Display control node 56 includes at least one display microcontroller that oversees the content displayed on a display 90 of at least one of the control panels 48. Display 90 may be positioned at any one or more of the three control panels 48*a*-*c*. As shown in FIG. 2, display 90 may take on a variety of different sizes, such as a display 90*a* having a 4.3 inch diagonal dimension, or a display 90*b* having an 8 inch diagonal dimension. Other sized displays can, of course, be used. In those embodiments of patient support apparatus 20 in which display 90 is implemented as a touchscreen, it also is configured to send commands and information back to main control node 52 indicating which touch screen controls have been activated by a user. In the particular embodiment of display control node 56 shown in FIG. 2, display control node 56 is in communication with a gateway node 92. Gateway node 92 includes one or more wired and/or wireless network transceivers (e.g. Ethernet port, USB port, ZigBee radio, and/or WiFi radio) adapted to communicate with both the local onboard network (e.g. a CAN network, a LIN network, etc.) and the healthcare facility's local area network and/or other electronic device(s) positioned off-board patient support apparatus 20. Certain data that is received via gateway node 92 from the off-board network is forwarded onto the local onboard network and processed by one or more of the node(s) 52-62 to which such data pertains, and gateway node 92 is further adapted to transmit selected traffic on the local network to one or more servers in communication with the healthcare facility's local area network and/or to one or more other off-board electronic devices. The operation of gateway node 92 is discussed in greater detail below.

Mattress control node 58 is adapted to control the operation of a powered mattress positioned on top of support deck 30. The powered mattress may take on a variety of different forms. In at least one embodiment, the powered mattress is constructed in accordance with any of the powered mattresses disclosed in either of the following commonly assigned U.S. Pat. No. 9,468,307 issued Oct. 18, 2016, to Lafleche et al. and entitled INFLATABLE MATTRESS AND CONTROL METHODS; and U.S. Pat. No. 9,782,312 issued Oct. 10, 2017, to Brubaker et al. and entitled PATIENT SUPPORT, the complete disclosures of both of which are incorporated herein by reference. Still other powered mattresses are able to be used. Further, in some embodiments, mattress control node 58 is adapted to control a plurality of different types of powered mattresses and includes a sensor for detecting the type of mattress supported on support deck 30.

When controlling the mattress positioned on top of support deck 30, mattress control node 58 communicates with the mattress by way of a serial cable that couples between mattress control node 58 and the mattress. In some embodiments, the serial cable is a USB cable, while in other embodiments a different type of cable is used. In still other embodiments, mattress control node 58 may wirelessly communicate with the mattress using any known wireless communication technique, including, but not limited to, inductive communication. One example of a mattress control board on a bed that uses inductive communication with a mattress positioned on top of the bed is disclosed in commonly assigned U.S. Pat. No. 9,289,336 issued Mar. 22, 2016, to inventors Clifford Lambarth et al. and entitled PATIENT SUPPORT WITH ENERGY TRANSPORT, the complete disclosure of which is incorporated herein by reference. Mattress control node 58 may be configured to implement the inductive communication techniques disclosed in this '336 patent.

Regardless of the physical communication method between mattress control node 58 and the powered mattress, mattress control node 58 is configured to put the mattress into at least two different states: a therapy state and a non-therapy state. In the therapy state, the mattress carries out one or more therapies on the patient, such as, but not limited to, rotational therapy, turning therapy, and/or percussion therapy. In the non-therapy state, the mattress does not carry out any therapies on the patient, but instead supports the patient in a cushioned manner.

Propulsion control node 60 controls an optional propulsion system that may or may not be included with patient support apparatus 20. When included, propulsion node 60 selectively drives at least one wheel of patient support apparatus 20 to thereby reduce the amount of effort required by a caregiver or other healthcare personnel when moving the patient support apparatus 20 from one location to another. Propulsion node 60 therefore is adapted to drive at least one propulsion motor 86 (FIG. 2) that drives at least one wheel of the patient support apparatus 20. Propulsion node 60 includes a propulsion user interface 94 that allows a caregiver to control the propulsion system (e.g. start, stop, accelerate, decelerate, steer, etc.), and a propulsion microcontroller that oversees the operation of the motor in response to the inputs received from user interface 94 and/or commands received from main control node 52.

Propulsion user interface 94 may take on a variety of different forms, but in at least one embodiment, it includes one or more handles with one or more sensors that, when pushed, drive the patient support apparatus 20. One example of a propulsion system and its user interface that is suitable for incorporation into patient support apparatus 20 is disclosed in commonly assigned U.S. patent application Ser. No. 15/471,361 filed Mar. 28, 2017, by inventors Thomas Puvogel et al. and entitled PATIENT SUPPORT APPARATUSES WITH DRIVE SYSTEMS, the complete disclosure of which is incorporated herein by reference. Another example of a propulsion system and its user interface that is suitable for incorporation into patient support apparatus 20 is disclosed in commonly assigned U.S. patent application Ser. No. 15/189,149 filed Jun. 22, 2016, by inventors Jerald Trepanier et al. and entitled PERSON SUPPORT APPARATUSES WITH DRIVE CONTROLS, the complete disclosure of which is also incorporated herein by reference. Still other types of propulsion systems and/or drive controls may be incorporated into patient support apparatus 20.

Room interface node 62 (FIG. 2) of control system 50 oversees communication between patient support apparatus 20 and one or more external devices integrated into a room 82 of the healthcare facility in which patient support apparatus 20 is currently located. Such external devices include a headwall outlet 96, a room light 98, and/or a television 100 positioned in the room (FIG. 3). In some embodiments, room interface node 62 may also be configured to communicate with a fixed locator (not shown) that emits a unique identifier that can be correlated to its location within the healthcare facility. Room interface node 62 also oversees communications between patient support apparatus 20 and a conventional nurse call system 106 of the healthcare facility.

Room interface node 62 may be implemented to carry out wired communication between the patient support apparatus 20 and headwall outlet 96, and/or it may be configured to carry out wireless communication between patient support apparatus 20 and headwall outlet 96. When configured for wired communication, a cable 88 typically is coupled between patient support apparatus 20 and headwall outlet 96 (FIG. 3). A plug 102 at one end of the cable 88 is coupled to headwall outlet 96, which is in communication with one or conductors 104 that communicatively couple the outlet 96 to light 98, television 100, and/or nurse call system 106. Further details regarding the communication between patient support apparatus 20 and headwall outlet 96, as well as examples of the structures that may be incorporated into room interface node 62, are disclosed in commonly assigned U.S. patent application Ser. No. 15/945,437 filed Apr. 4, 2018, by inventors Krishna Bhimavarapu et al. and entitled PATIENT SUPPORT APPARATUSES WITH RECONFIGURABLE COMMUNICATION, the complete disclosure of which is incorporated herein by reference.

When room interface node 62 communicates wirelessly with nurse call system 106, it is configured to wirelessly communicate with a wall module that is physically coupled to the headwall outlet 96 via a cable. Such communication takes place, in at least some embodiments, via a Bluetooth transceiver (FIG. 3) incorporated into, or otherwise in communication with, room interface node 62. Suitable examples of wall modules with which room interface node 62 can wirelessly communicate are the headwall interfaces 38 disclosed in commonly assigned U.S. patent publication 2016/0038361 published Feb. 11, 2016, by inventors Krishna Bhimavarapu et al. and entitled PATIENT SUPPORT APPARATUSES WITH WIRELESS HEADWALL COMMUNICATION, the complete disclosure of which is incorporated herein by reference. Additional functions and/or structures that may be performed by, or included with, room interface node 62 when wirelessly communicating with a wall module are disclosed in the following commonly assigned patent references and may be implemented in patient support apparatus 20 herein: U.S. patent application Ser. No. 62/600,000 filed Dec. 18, 2017, by inventor Alexander J. Bodurka and entitled SMART HOSPITAL HEADWALL SYSTEM; U.S. patent application Ser. No. 62/587,867 filed Nov. 17, 2017, by inventors Alexander J. Bodurka et al. and entitled PATIENT SUPPORT APPARATUSES WITH LOCATION/MOVEMENT DETECTION; U.S. patent application Ser. No. 16/847,753 filed Apr. 14, 2020, by inventors Alexander Bodurka et al. and entitled PATIENT SUPPORT APPARATUSES WITH NURSE CALL AUDIO MANAGEMENT; U.S. patent application Ser. No. 63/026,937 filed May 19, 2020, by inventors Alexander Bodurka et al. and entitled PATIENT SUPPORT APPARATUSES WITH HEADWALL COMMUNICATION; and U.S. patent application Ser. No. 62/598,787 filed Dec. 14, 2017, by inventors Alexander J. Bodurka et al. and entitled HOSPITAL HEADWALL COMMUNICATION SYSTEM, the complete disclosures of all of which are incorporated herein by reference. Still other types of wireless communication with a headwall outlet 96 may, of course, be used.

Room interface node 62 also is adapted, in some embodiments, to communicate with a fixed locator that is mounted at a known location and generally within close proximity to patient support apparatus 20 (e.g. with a few meters, generally speaking). In some embodiments, the fixed locator is integrated into the wall module discussed above (including many of the patent references incorporated herein by reference). Further details of the operation of at least one embodiment of the fixed locators and their interaction with patient support apparatus 20 can be found in commonly assigned, U.S. patent application Ser. No. 12/573,545 filed Oct. 5, 2009 by applicants David Becker et al. and entitled LOCATION DETECTION SYSTEM FOR A PATIENT HANDLING DEVICE and U.S. patent application Ser. No. 15/909,131 filed Mar. 1, 2018 by applicants Michael Joseph Hayes et al. and entitled PATIENT SUPPORT APPARATUS COMMUNICATION SYSTEMS, the complete disclosures of which are also incorporated by reference herein. The fixed locators may also take on any of the forms, and perform any of the functions, disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION; Ser. No. 16/217,203 filed Dec. 12, 2018, by inventor Alex Bodurka, and entitled SMART HOSPITAL HEADWALL SYSTEM; Ser. No. 16/193,150 filed Nov. 16, 2018, by inventors Alexander Bodurka et al. and entitled PATIENT SUPPORT APPARATUSES WITH LOCATION/MOVEMENT DETECTION; and Ser. No. 16/215,911 filed Dec. 11, 2018, by inventors Alex Bodurka et al. and entitled HOSPITAL HEADWALL COMMUNICATION SYSTEM, the complete disclosures of all of which are incorporated herein by Inner and outer siderail boards 64 and 66 (FIG. 2) are adapted to control the corresponding inner and outer control panels 48*b* and 48*c*. As was noted previously, each of the control panels 48*a-c* includes a plurality of user controls for controlling various functions of the patient support apparatus 20. One or more of the controls panels 48*a-c* may also or alternatively include a display 90. When included, display 90 is a touch screen display in at least some embodiments, although it will be understood that a non-touch screen display 90 may alternatively be used. It will also be understood that any of the control panels 48*a-c* may be implemented without any display at all. The controls of control panels 48*a-c* can be touch sensitive controls that may be physically implemented in a variety of different manners. In some embodiments, the controls are implemented as capacitive sensors positioned adjacent display 90 that capacitively detect when a user presses them. In other embodiments, the controls are implemented as buttons, switches, or other types of force or touch-sensitive devices. In still other embodiments, one or more of controls may be incorporated into the touchscreen display 90. Still other variations are possible.

The controls of control panels 48*a-c* include controls for raising/lowering the litter frame 28, changing the position of a section 40-46 of the support deck 30, activating/deactivating a brake, controlling a scale/exit detection system (e.g. taking a weight reading, arming an exit detection system, etc.), locking out one or more functions, setting an alert, inputting patient information and/or therapy data (e.g. a prescribed turning frequency, etc.), and/or other controls. At least one of the inner control panels 48*b* also include a nurse call button, as well as a speaker and microphone, which collectively enable the patient to call and talk to a remotely positioned nurse, such as a nurse located at a corresponding nurses' station 118 within the healthcare facility.

Siderail control boards 64 and 66 may each include siderail microcontrollers that process the controls activated by a user and send appropriate messages to main control node 52 in response to the activation of the controls. For example, if a user presses a control dedicated to raising head section 40, the siderail microcontroller of control board 64 (if inner control panel 48*b* was activated) or the siderail microcontroller of control board 66 (if outer control panel 48*c* was activated) sends a message to main control node 52 instructing it to raise the head section 40. Main control node 52 forwards the message to motion control node 54 which, in turn, sends the appropriate control signals to the motorized actuator 84*a*, thereby causing motorized actuator 84*a* to raise head section 40. Alternatively, the microcontroller of siderail control boards 64 or 66 may send a motion control message directly to motion control node 54 in response to a user activating the control for raising the head section 40, thereby avoiding the need for main control node 52 to act as an intermediary between boards 64 (or 66) and motion control node 54. Siderail control boards 64 and 66 may also control the illumination of controls, any audio and/or visual alerting structures built into siderails 34, a USB port 108 (FIG. 2), and the microphone and speakers. USB port 108, if included, allows a patient to charge any USB compatible personal electronic devices he or she may possess while positioned on support deck 30. One example of the functional and/or structural design of USB port 108 that may be incorporated into patient support apparatus 20 is disclosed in commonly assigned U.S. patent application Ser. No. 16/035,156 filed Jul. 13, 2018, by inventors Krishna Bhimavarapu et al. and entitled PATIENT SUPPORT APPARATUSES WITH PERSONAL ELECTRONIC DEVICE CHARGING, the complete disclosure of which is incorporated herein by reference.

As noted previously, main control node 52 is in communication with night light 68, a brake switch 70, and an electric brake 72. Night light 68, when activated, provides illumination to an adjacent area of the floor, thereby helping a patient to navigate during low light conditions. Brake switch 70 is a sensor that sends a signal to main control node 52 indicating whether the brake of patient support apparatus 20 is currently activated or not. The brake resists movement of patient support apparatus 20 when activated. In some embodiments, the activation of the brake applies a braking force to all of wheels 24, while in other embodiments, the activation of the brake applies a braking force to a subset of the wheels 24 and/or to one or more other wheels on patient support apparatus 20. Electric brake 72 is an electrical actuator that allows a user to electrically activate the brake through a corresponding control positioned on one or more of control panels 48*a-c*. Electric brake 72 is often accompanied by a manual actuator such as, but not limited to, one or more pedals, thereby giving the user the option of manually and mechanically actuating the brake or electrically actuating the brake. In some embodiments, electric brake 72 is constructed in accordance with the electric brake disclosed in commonly assigned U.S. Pat. No. 8,701,229 issued Apr. 22, 2014, to inventors Guy Lemire et al. and entitled HOSPITAL BED, the complete disclosure of which is incorporated herein by reference. Still other types of electric brakes may, of course, be used.

Main control node 52 is adapted to communicate with a patient pendant 74 that may be coupled to patient support apparatus 20. The patient pendant 74, when included, plugs into a port in communication with main control node 52 and includes one or more controls for controlling various aspects of patient support apparatus 20. The patient pendant 74 may also include a speaker and microphone, thereby enabling the pendant 74 to be used as a communication device for communicating with a remotely positioned nurse (via the nurse call system and room interface node 62, as described previously).

Load cells 80 feed into main control node 52. Load cells 80 are configured to support litter frame 28. More specifically, load cells 80 are configured such that they provide complete mechanical support for litter frame 28 and all of the components that are supported on litter frame 28 (e.g. support deck 30, footboard 32, the headboard, siderails 34, etc.). Because of this construction, load cells 80 detect the weight of not only those components of patient support apparatus 20 that are supported by litter frame 28 (including litter frame 28 itself), but also any objects or persons who are wholly or partially being supported by support deck 30. Load cells 80 are adapted to detect downward forces exerted by an occupant of support deck 30. Thus, when an occupant is positioned on support deck 30 and substantially still (i.e. not moving in a manner involving accelerations that cause forces to be exerted against support deck 30), load cells 80 detect the weight of the occupant (as well as the weight of any components of patient support apparatus 20 that are supported—directly or indirectly—by load cells 80).

The outputs of load cells 80 are processed by main control node 52 in order to implement a scale function and/or an exit detection function. When implementing the scale function, main control node 52 sums the outputs of the load cells 80 to determine a weight of the patient. When implementing the exit detection function, main control node 52 processes the outputs of the load cells 80 to detect when an occupant has exited the patient support apparatus 20, or when an occupant may be about to exit the patient support apparatus 20. One exemplary manner of processing the outputs of load cells 80 to implement an exit detection function and/or a scale function is described in U.S. Patent Application Pub. No. 2017/0003159, filed on Jun. 17, 2016, entitled PERSON SUPPORT APPARATUS WITH LOAD CELLS, which is hereby incorporated by reference herein in its entirety. Another exemplary exit detection function that may be incorporated into patient support apparatus 20 is described in U.S. Pat. No. 5,276,432, filed on Jan. 15, 1992, entitled PATIENT EXIT DETECTION MECHANISM FOR HOSPITAL BED, which is hereby incorporated by reference herein in its entirety. Other types of scale and/or exit detection functionality and/or algorithms may be used.

In some embodiments, load cells 80 may be replaced with linear variable displacement transducers and/or any one or more capacitive, inductive, and/or resistive transducers that are configured to produce a changing output in response to changes in the force exerted against them. Still other types of forces sensors may be used with patient support apparatus 20 in lieu of, or in addition to, load cells 80.

Power supply 76 is electrically coupled to an outlet plug 110 (FIG. 2) that is adapted to be inserted into a conventional wall power outlet. That is, power supply 76 is adapted to receive electrical power from a mains source of electricity and to deliver that power to the main control board. As shown in FIG. 2, the power received by plug 110 passes through an inlet filter 112 (such as an IEC 320 style inlet filter) and a circuit breaker 114 before being delivered to power supply 76. Inlet filter 112 may include a fuse and/or other circuitry for limiting the amount of electrical power delivered to control system 50. Circuit breakers 114 protect power supply 76 and the rest of control system 50 from excessive voltage and/or current by interrupting the current flow to power supply 76 when such a condition is detected.

Power supply 76 performs a number of functions including, but not limited to, rectifying the incoming main power from AC to DC, down converting the incoming voltage to a suitable voltage (e.g. 36 volts), providing overcurrent and/or overvoltage protection, reducing and/or eliminating power noise, and the like. Power supply 76 and control system 50 may include any of the structures and/or functionality of the power supply and control system disclosed in commonly assigned U.S. patent application Ser. No. 16/828,323 filed Mar. 24, 2020, by inventors Zane Shami et al. and entitled PATIENT CARE SYSTEM WITH POWER MANAGEMENT, the complete disclosure of which is incorporated herein by reference.

In some embodiments, patient support apparatus 20 communicates with a patient support apparatus server 120 (FIG. 3) via one or more wireless access points 122 positioned throughout a typical healthcare facility and in communication with the healthcare facility's local area network 124. In some embodiments, the patient support apparatus server 120 is a server commercially offered for sale by Stryker Medical of Kalamazoo, Mich., such as, but not limited to, the Stryker iBed Server 2.0, which is described in more detail in the Stryker Installation/Configuration Manual for the iBed Server 2.0, Connected Hospital®, Model 5212, published in 2016 (document 5212-209-001 Rev A), the complete disclosure of which is incorporated herein by reference. In other embodiments, the patient support apparatus server 120 is a different type of server. Regardless of its specific type, patient support apparatus server 120 coordinates communications between the various patient support apparatuses 20 in a healthcare facility and any of the other applications or servers that are present on the local area network. Thus, patient support apparatus server 120 receives communications from patient support apparatuses 20 and then forwards—or makes available—information from those communications to selected entities on the local area network, as appropriate.

Healthcare facility computer network 124 typically includes a plurality of servers, such as, but not limited to, an Electronic Medical Records (EMR) server, an Admission, Discharge, and Transfer (ADT) server, a mobile communication server, and/or other servers 126 (FIG. 3). One or more network appliances 128 may also be present that act as an Internet gateway that couples network 124 to the Internet 130, thereby enabling server 120, patient support apparatuses 20, and/or other applications on network 124 to communicate with computers outside of the healthcare facility, such as, but not limited to, a geographically remote server 132 operated under the control of the manufacturer of patient support apparatuses 20. Another type of server that may be included with computer network 124 is a location server (not shown) that is adapted to monitor and record the current locations of patient support apparatuses 20, patients, and/or caregivers within the healthcare facility. Such a location server communicates with the patient support apparatuses 20 via access points 122 and gateway node 92.

Network 124 may also include a one or more conventional work flow servers and/or charting servers that assign, monitor, and/or schedule patient-related tasks to particular caregivers, and/or one or more conventional communication servers that forward communications to particular individuals within the healthcare facility, such as via one or more portable devices (smart phones, pagers, beepers, laptops, etc.). The forwarded communications may include data and/or alerts that originate from patient support apparatuses 20. In some embodiments, server 120 and/or another server on network 124 is adapted to execute a caregiver assistance application that communicates with patient support apparatuses 20 and mobile electronic devices carried by caregivers, thereby enabling the caregivers to receive information about the state of the patient support apparatuses assigned to them, as well as perform other tasks. In one embodiment, patient support apparatus server 120 is adapted to execute, or is in communication with another server that executes, a caregiver assistance application having the functionality of the caregiver assistance application disclosed in commonly assigned PCT patent application number PCT/US2020/039587 filed Jun. 25, 2020, by applicant Stryker Corporation and entitled CAREGIVER ASSISTANCE SYSTEM, the complete disclosure of which is incorporated herein by reference.

In the illustrated embodiment, each node 52-62, 92 is coupled together by one or more conductors 116 (FIG. 2). Conductors 116 enable data to be transferred between nodes 52-62, 92. The conductors 116 and nodes 52-62, 92 together form a local, onboard network 146. In some embodiments, each conductor 116 includes a multi-pin connector wherein at least two of the pins are used for data communication (e.g. CAN High and CAN Low), at least one pin is used for power high, and at least one pin is used for power low (e.g. ground). Additional pins may be present for sending addition data and/or other signals that are not communicated over the embedded network connection (e.g. the CAN network). As noted, for many components, the data connections comprise a CAN bus, although it will be understood that other communication protocols can be used, such as, but not limited to, a Local Interconnect Network (LIN) bus, an Ethernet, an I-Squared-C bus, and/or another type of communication technology. For those components that do not utilize a microcontroller (e.g. night light 68, brake switch 70, electric brake 72, load cells 80), the data connection between themselves and their connected node may be a Serial Peripheral Interface (SPI), I2C, or other type of connection. Still other types of communication protocols and/or connections may be used.

The microcontrollers of nodes 52-62, 92 may be microcontrollers from the Kinetis MK66F family of microcontrollers manufactured by NXP semiconductors of Eindhoven, the Netherlands, such as, but not limited to, the Kinetis MK66FN2MOVLQ18 microcontroller. Other microcontrollers can, of course be used. In general, each of the nodes 52-62, 92 include, in addition to the microcontrollers discussed herein, additional circuitry and programming for carrying out the functions described herein, as would be known to one of ordinary skill in the art. Such additional circuitry may include, but is not limited to, field programmable gate arrays, volatile or nonvolatile memory, discrete circuitry, and/or other hardware, software, or firmware that is capable of carrying out the functions described herein. The components of each board can be physically configured in any suitable manner, such as by mounting them all to a single circuit board, or they can be distributed across multiple circuit boards. The instructions followed by each of the microcontrollers in carrying out the functions described herein, as well as the data necessary for carrying out these functions, are stored in memories (not labeled in FIG. 2) mounted to each of the circuit boards associated with the nodes, or otherwise accessible to each microcontroller.

Figure 4:
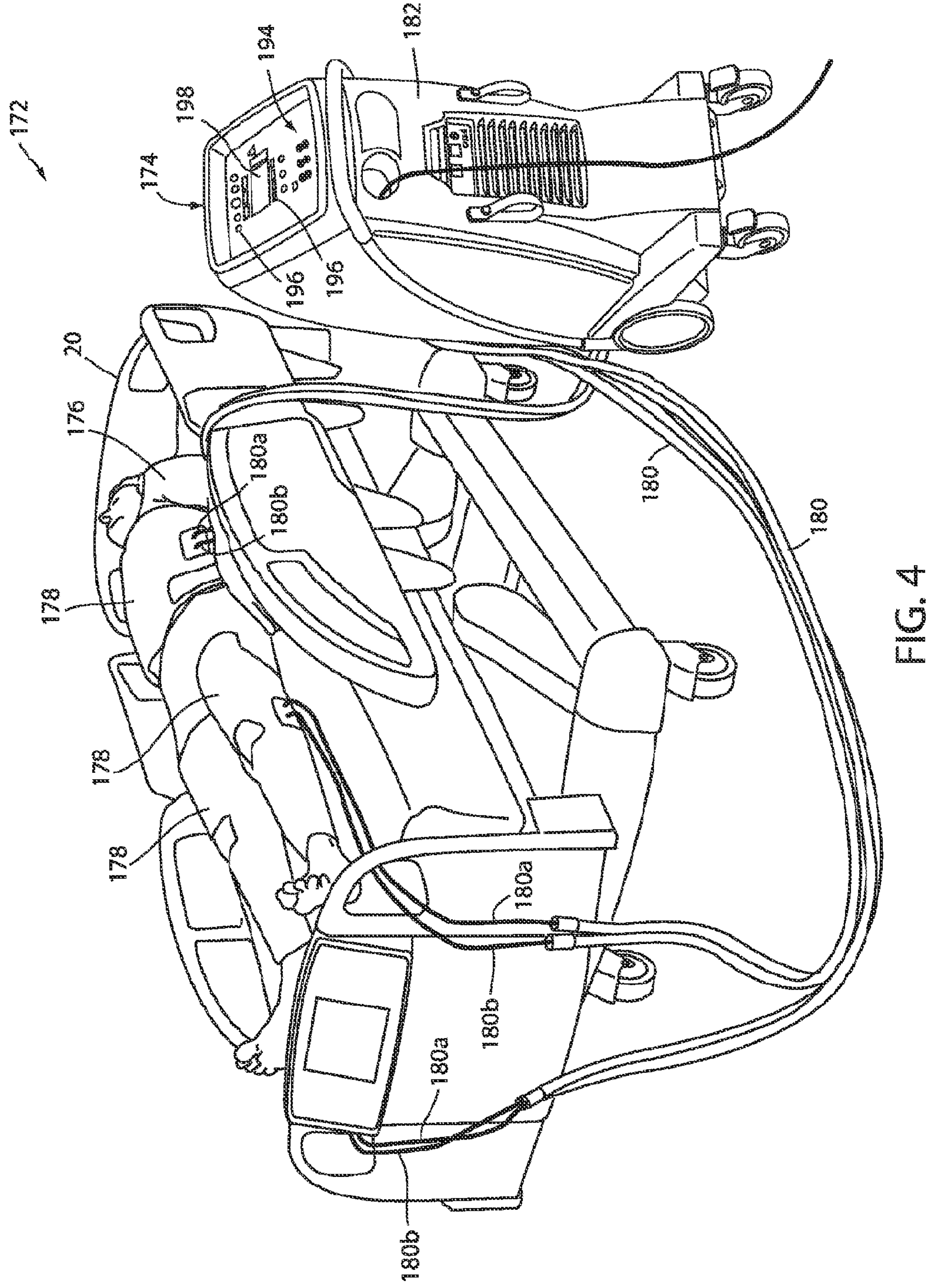
FIG. 4 is a perspective view of a thermal control unit into which one or more features of the present disclosure may be incorporated.

A thermal control system 172 according to one embodiment of the present disclosure is shown in FIG. 4. Thermal control system 172 is adapted to control the temperature of a patient 176, which may involve raising, lowering, and/or maintaining the patient's temperature. Thermal control system 172 includes a thermal control unit 174 coupled to one or more thermal therapy devices 178. The thermal therapy devices 178 are illustrated in FIG. 4 to be thermal pads, but it will be understood that thermal therapy devices 178 may take on other forms, such as, but not limited to, blankets, vests, patches, caps, catheters, or other structures that receive temperature-controlled fluid. For purposes of the following written description, thermal therapy devices 178 will be referred to as thermal pads 178, but it will be understood by those skilled in the art that this terminology is used merely for convenience and that the phrase "thermal pad" is intended to cover all of the different variations of thermal therapy devices 178 mentioned above (e.g. blankets, vests, patches, caps, catheters, etc.) and variations thereof.

Thermal control unit 174 is coupled to thermal pads 178 via a plurality of hoses 180. Thermal control unit 174 delivers temperature-controlled fluid (such as, but not limited to, water or a water mixture) to the thermal pads 178 via the fluid supply hoses 180*a*. After the temperature-controlled fluid has passed through thermal pads 178, thermal control unit 174 receives the temperature-controlled fluid back from thermal pads 178 via the return hoses 180*b*.

In the embodiment of thermal control system 172 shown in FIG. 4, three thermal pads 178 are used in the treatment of patient 176. A first thermal pad 178 is wrapped around a patient's torso, while second and third thermal pads 178 are wrapped, respectively, around the patient's right and left legs. Other configurations can be used and different numbers of thermal pads 178 may be used with thermal control unit 174, depending upon the number of inlet and outlet ports that are included with thermal control unit 174. By controlling the temperature of the fluid delivered to thermal pads 178 via supply hoses 180*a*, the temperature of the patient 176 can be controlled via the close contact of the pads 178 with the patient 176 and the resultant heat transfer therebetween.

Figure 5:
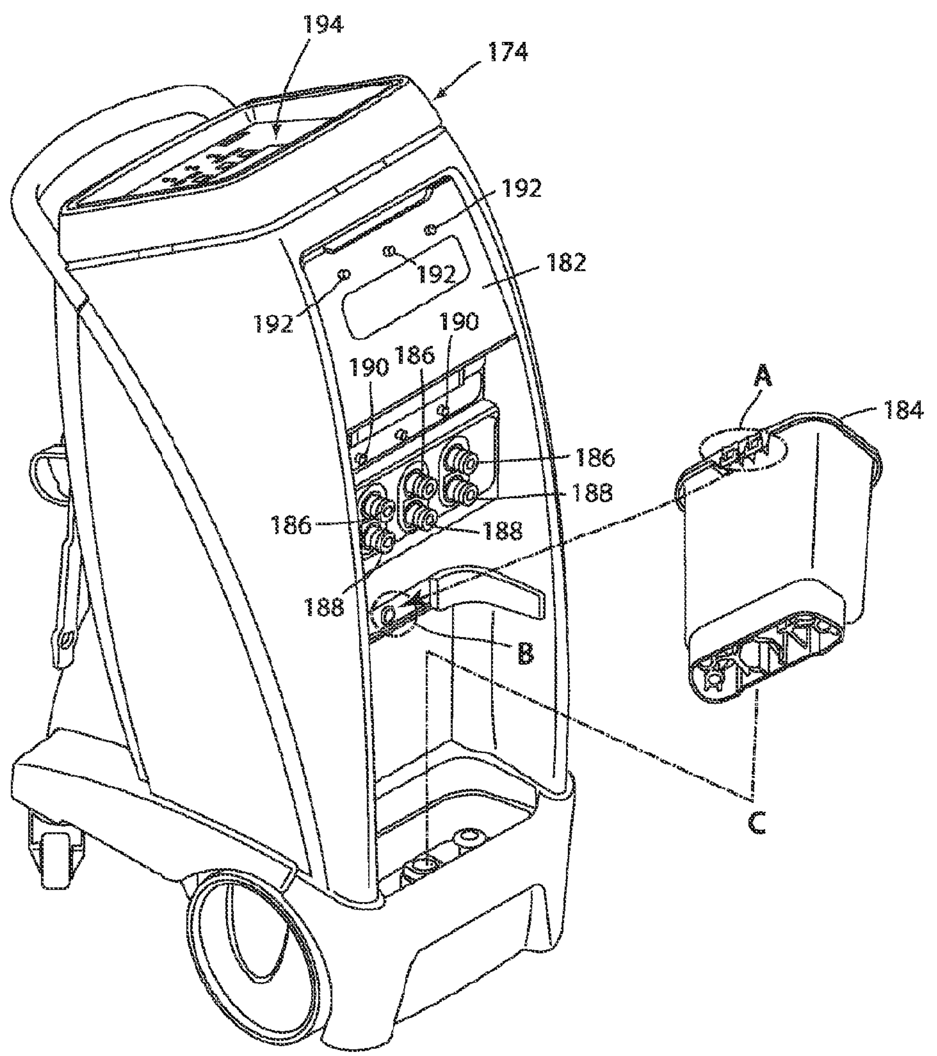
FIG. 5 is a perspective view of the thermal control unit of FIG. 4 shown from another angle.

As shown more clearly in FIG. 5, thermal control unit 174 includes a main body 182 to which a removable reservoir 184 may be coupled and uncoupled. Removable reservoir 184 is configured to hold the fluid that is to be circulated through thermal control unit 174 and the one or more thermal pads 178. By being removable from thermal control unit 174, reservoir 184 can be easily carried to a sink or faucet for filling and/or dumping of the water or other fluid. This allows users of thermal control system 172 to more easily fill thermal control unit 174 prior to its use, as well as to drain thermal control unit 174 after use.

As can also be seen in FIG. 4, thermal control unit 174 includes a plurality of outlet ports 186 (three in the particular example of FIG. 4), a plurality of inlet ports 188 (three in this particular example). Outlet ports 186 are adapted to fluidly couple to supply hoses 180 and inlet ports 188 are adapted to fluidly couple to return hoses 180*b*. Thermal control unit 174 also includes a plurality of patient temperature probe ports 190, a plurality of auxiliary ports 192, and a control panel 194 having a plurality of dedicated controls 196 and a display 198. The patient temperature probe ports 190, auxiliary ports 192, and control panel 194 are described in more detail below.

Figure 6:
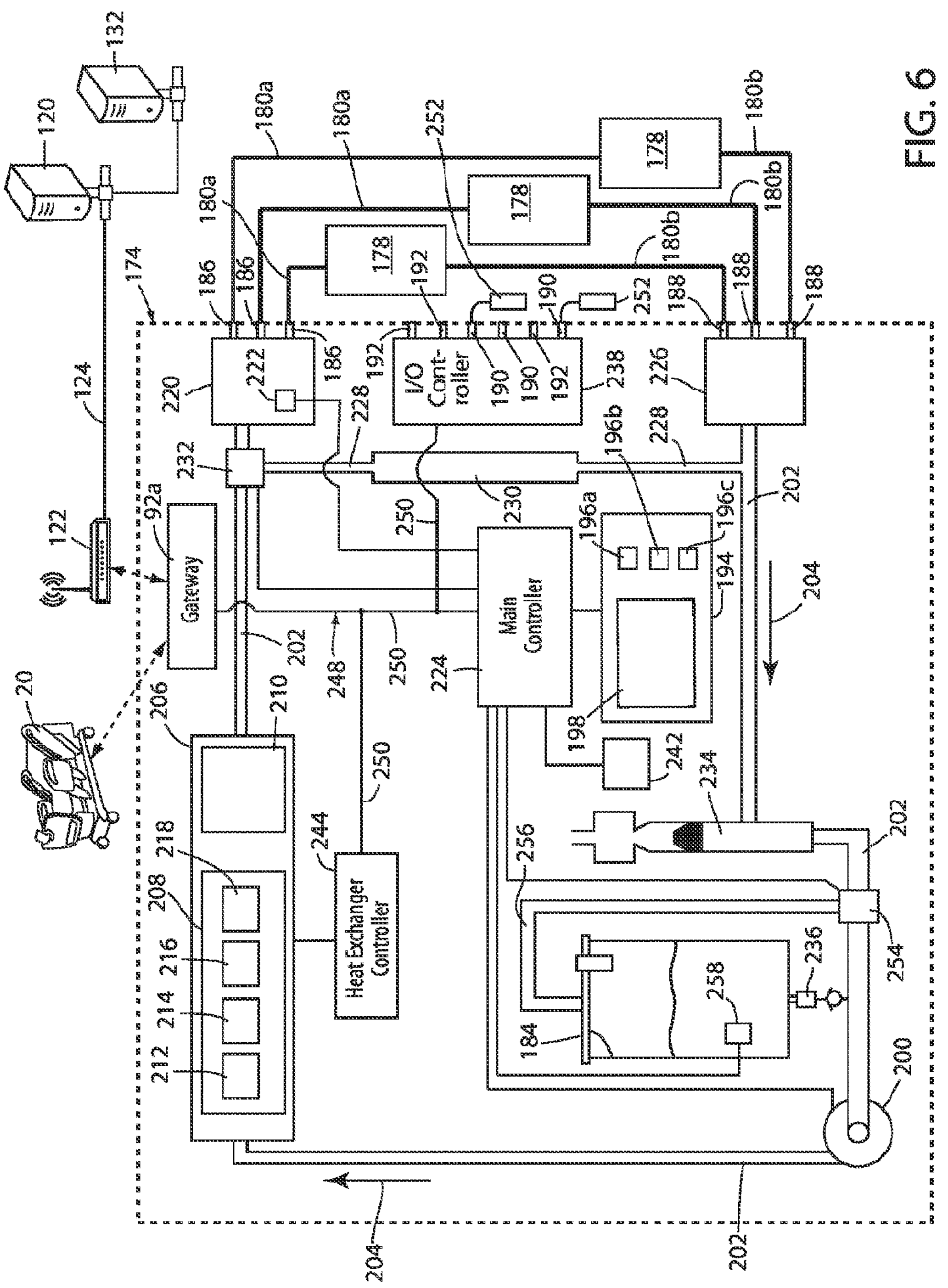
FIG. 6 is a block diagram of a control system that may be used with the thermal control unit of FIG. 4.

As shown in FIG. 6, thermal control unit 174 includes a pump 200 for circulating fluid through a circulation channel 202. Pump 200, when activated, circulates the fluid through circulation channel 202 in the direction of arrows 204 (clockwise in FIG. 6). Starting at pump 200 the circulating fluid first passes through a heat exchanger 206 that adjusts, as necessary, the temperature of the circulating fluid. Heat exchanger 206 may take on a variety of different forms. In some embodiments, heat exchanger 206 is a thermoelectric heater and cooler. In the embodiment shown in FIG. 6, heat exchanger 206 includes a chiller 208 and a heater 210. Further, in the embodiment shown in FIG. 6, chiller 208 is a conventional vapor-compression refrigeration unit having a compressor 212, a condenser 214, an evaporator 216, an expansion valve (not shown), and a fan 218 for removing heat from the compressor 212. Heater 210 is a conventional electrical resistance-based heater. Other types of chillers and/or heaters may be used.

After passing through heat exchanger 206, the circulating fluid is delivered to an outlet manifold 220 having an outlet temperature sensor 222 and a plurality of outlet ports 186. Temperature sensor 222 is adapted to detect a temperature of the fluid inside of outlet manifold 220 and report it to a main controller 224. Outlet ports 186 are coupled to supply hoses 180*a*. Supply hoses 180*a* are coupled, in turn, to thermal pads 178 and deliver temperature-controlled fluid to the thermal pads 178. The temperature-controlled fluid, after passing through the thermal pads 178, is returned to thermal control unit 174 via return hoses 180*b*. Return hoses 180*b* couple to a plurality of inlet ports 188. Inlet ports 188 are fluidly coupled to an inlet manifold 226 inside of thermal control unit 174.

Thermal control unit 174 also includes a bypass line 228 fluidly coupled to outlet manifold 220 and inlet manifold 226 (FIG. 6). Bypass line 228 allows fluid to circulate through circulation channel 202 even in the absence of any thermal pads 178 or hoses 180*a* being coupled to any of outlet ports 186. In the illustrated embodiment, bypass line 228 includes an optional filter 230 that is adapted to filter the circulating fluid. If included, filter 230 may be a particle filter adapted to filter out particles within the circulating fluid that exceed a size threshold, or filter 230 may be a biological filter adapted to purify or sanitize the circulating fluid, or it may be a combination of both. In some embodiments, filter 230 is constructed and/or positioned within thermal control unit 174 in any of the manners disclosed in commonly assigned U.S. patent application Ser. No. 62/404,676 filed Oct. 11, 2016, by inventors Marko Kostic et al. and entitled THERMAL CONTROL SYSTEM, the complete disclosure of which is incorporated herein by reference.

The flow of fluid through bypass line 228 is controllable by way of a bypass valve 232 positioned at the intersection of bypass line 228 and outlet manifold 220 (FIG. 6). When open, bypass valve 232 allows fluid to flow through circulation channel 202 to outlet manifold 220, and from outlet manifold 220 to the connected thermal pads 178. When closed, bypass valve 232 stops fluid from flowing to outlet manifold 220 (and thermal pads 178) and instead diverts the fluid flow along bypass line 228. In some embodiments, bypass valve 232 may be controllable such that selective portions of the fluid are directed to outlet manifold 220 and along bypass line 228. In some embodiments, bypass valve 232 is controlled in any of the manners discussed in commonly assigned U.S. patent application Ser. No. 62/610,319, filed Dec. 26, 2017, by inventors Gregory Taylor et al. and entitled THERMAL SYSTEM WITH OVERSHOOT REDUCTION, the complete disclosure of which is incorporated herein by reference. In other embodiments, bypass valve 232 may be a pressure operated valve that allows fluid to flow along bypass line 228 if the fluid pressure in circulation channel 202 exceeds the cracking pressure of the bypass valve 232. Still further, in some embodiments, bypass valve 232 may be omitted and fluid may be allowed to flow through both bypass line 228 and into outlet manifold 220.

The incoming fluid flowing into inlet manifold 226 from inlet ports 188 and/or bypass line 228 travels back toward pump 200 and into an air remover 234. Air remover 234 includes any structure in which the flow of fluid slows down sufficiently to allow air bubbles contained within the circulating fluid to float upwardly and escape to the ambient surroundings. In some embodiments, air remover 234 is constructed in accordance with any of the configurations disclosed in commonly assigned U.S. patent application Ser. No. 15/646,847 filed Jul. 11, 2017, by inventor Gregory S. Taylor and entitled THERMAL CONTROL SYSTEM, the complete disclosure of which is hereby incorporated herein by reference. After passing through air remover 234, the circulating fluid flows past a valve 236 positioned beneath fluid reservoir 184. Fluid reservoir 184 supplies fluid to thermal control unit 174 and circulation channel 202 via valve 236, which may be a conventional check valve, or other type of valve, that automatically opens when reservoir 184 is coupled to thermal control unit 174 and that automatically closes when reservoir 184 is decoupled from thermal control unit 174 (see FIG. 5). After passing by valve 236, the circulating fluid travels to pump 200 and the circuit is repeated.

Main controller 224 of thermal control unit 174 is contained within main body 182 of thermal control unit 174 and is in electrical communication with pump 200, heat exchanger 206, outlet temperature sensor 222, bypass valve 232, an input/output controller 238, control panel 194, a heat exchanger controller 244, a gateway 92*a*, and, in some embodiments, a location sensor 242. Main controller 224, input/output (I/O) controller 238, heat exchanger controller 244, and gateway 92*a* are nodes of an onboard network 248. In the illustrated embodiment, each node 224, 238, 244, and 92*a* are coupled together by one or more conductors 250 (FIG. 6). Conductors 250 enable data to be transferred between nodes 224, 238, 244, and 92*a*. The conductors 250 and nodes 224, 238, 244, and 92*a* together form the local, onboard network 248. In some embodiments, each conductor 250 includes a multi-pin connector wherein at least two of the pins are used for data communication (e.g. CAN High and CAN Low), at least one pin is used for power high, and at least one pin is used for power low (e.g. ground). Additional pins may be present for sending addition data and/or other signals that are not communicated over the embedded network connection (e.g. the CAN network). As noted, for many components, the data connections comprise a CAN bus, although it will be understood that other communication protocols can be used, such as, but not limited to, a Local Interconnect Network (LIN) bus, an Ethernet, an I-Squared-C bus, and/or another type of communication technology. For those components that do not utilize a microcontroller (e.g. valve 232, temperature sensor 222, pump 200, a reservoir temperature sensor 258, etc.), the data connection between themselves and their connected node may be a Serial Peripheral Interface (SPI), 12C, or other type of connection. Still other types of communication protocols and/or connections may be used.

Main controller 224, I/O controller 238, and heat exchanger controller 244 includes any and all electrical circuitry and components necessary to carry out the functions and algorithms described herein, as would be known to one of ordinary skill in the art. Generally speaking, Main controller 224, I/O controller 238, and heat exchanger controller 244 may include one or more microcontrollers, microprocessors, and/or other programmable electronics that are programmed to carry out the functions described herein. It will be understood that Main controller 224, I/O controller 238, and heat exchanger controller 244 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 174, or they may reside in a common location within thermal control unit 174. When physically distributed, the components may communicate using any suitable serial or parallel communication protocol, such as, but not limited to, CAN, LIN, Firewire, I-squared-C, RS-232, RS-465, universal serial bus (USB), etc.

Control panel 194 allows a user to operate thermal control unit 174. Control panel 194 communicates with main controller 224 and includes display 198 and a plurality of dedicated controls 196*a*, 196*b*, 196*c*, etc. Display 198 may be implemented as a touch screen, or, in some embodiments, as a non-touch-sensitive display. Dedicated controls 196 may be implemented as buttons, switches, dials, or other dedicated structures. In any of the embodiments, one or more of the functions carried out by a dedicated control 196 may be replaced or supplemented with a touch screen control that is activated when touched by a user. Alternatively, in any of the embodiments, one or more of the controls that are carried out via a touch screen can be replaced or supplemented with a dedicated control 196 that carries out the same function when activated by a user.

Through either dedicated controls 196 and/or a touch screen display (e.g. display 198), control panel 194 enables a user to turn thermal control unit 174 on and off, select a mode of operation, select a target temperature for the fluid delivered to thermal pads 178, select a patient target temperature, and control other aspects of thermal control unit 174. In some embodiments, control panel 194 may include a pause/event control, a medication control, and/or an automatic temperature adjustment control that operate in accordance with the pause event control 66*b*, medication control 66*c*, and automatic temperature adjustment control 66*d* disclosed in commonly assigned U.S. patent application Ser. No. 62/577,772 filed on Oct. 27, 2017, by inventors Gregory Taylor et al. and entitled THERMAL SYSTEM WITH MEDICATION INTERACTION, the complete disclosure of which is incorporated herein by reference. Such controls may be activated as touch screen controls or dedicated controls 196.

In those embodiments where control panel 194 allows a user to select from different modes for controlling the patient's temperature, the different modes include, but are not limited to, a manual mode and an automatic mode, both of which may be used for cooling and heating the patient. In the manual mode, a user selects a target temperature for the fluid that circulates within thermal control unit 174 and that is delivered to thermal pads 178. Thermal control unit 174 then makes adjustments to heat exchanger 206 in order to ensure that the temperature of the fluid exiting supply hoses 180*a* is at the user-selected temperature.

Another one of the modes is an automatic mode. When the user selects the automatic mode, the user selects a target patient temperature, rather than a target fluid temperature. After selecting the target patient temperature, main controller 224 makes automatic adjustments to the temperature of the fluid in order to bring the patient's temperature to the desired patient target temperature. In this mode, the temperature of the circulating fluid may vary as necessary in order to bring about the target patient temperature.

In order to carry out the automatic mode, thermal control unit 174 utilizes I/O controller 238. I/O controller 238 includes one or more patient temperature sensor ports 190 (FIG. 5) that are adapted to receive one or more conventional patient temperature sensors or probes 252. The patient temperature sensors 252 may be any suitable patient temperature sensor that is able to sense the temperature of the patient at the location of the sensor. In one embodiment, the patient temperature sensors are conventional Y.S.I. 400 probes marketed by YSI Incorporated of Yellow Springs, Ohio, or probes that are YSI 400 compliant or otherwise marketed as 400 series probes. In other embodiments, different types of sensors may be used with thermal control unit 174. Regardless of the specific type of patient temperature sensor used in thermal control system 172, each temperature sensor 252 is connected to a patient temperature sensor port 190 positioned on thermal control unit 174. Patient temperature sensor ports 190 are in electrical communication with main controller 224 and provide current temperature readings of the patient's temperature.

Main controller 224, in some embodiments, controls the temperature of the circulating fluid using closed-loop feedback from temperature sensor 222. That is, main controller 224 determines (or receives) a target temperature of the fluid, compares it to the measured temperature from sensor 222, and issues a command to heat exchanger controller 244, which in turn controls heat exchanger 206 in a manner that seeks to decrease the difference between the desired fluid temperature and the measured fluid temperature. In some embodiments, the difference between the fluid target temperature and the measured fluid temperature is used as an error value that is input into a conventional Proportional, Integral, Derivative (PID) control loop. That is, main controller 224 or heat exchanger controller 244 multiplies the fluid temperature error by a proportional constant, determines the derivative of the fluid temperature error over time and multiplies it by a derivative constant, and determines the integral of the fluid temperature error over time and multiplies it by an integral constant. The results of each product are summed together and converted to a heating/cooling command that is fed to heat exchanger 206 and tells heat exchanger 206 whether to heat and/or cool the circulating fluid and how much heating/cooling power to use.

When thermal control unit 174 is operating in the automatic mode, main controller 224 or heat exchanger controller 244 may use a second closed-loop control loop that determines the difference between a patient target temperature and a measured patient temperature. The patient target temperature is input by a user of thermal control unit 174 using control panel 194. The measured patient temperature comes from a patient temperature sensor 252 coupled to one of patient temperature sensor ports 190 (FIGS. 5, 6). Main controller 224 or heat exchanger controller 244 determines the difference between the patient target temperature and the measured patient temperature and, in some embodiments, uses the resulting patient temperature error value as an input into a conventional PID control loop. As part of the PID loop, main controller 224 or heat exchanger controller 244 multiplies the patient temperature error by a proportional constant, multiplies a derivative of the patient temperature error over time by a derivative constant, and multiplies an integral of the patient temperature error over time by an integral constant. The three products are summed together and converted to a target fluid temperature value. The target fluid temperature value is then fed to the first control loop discussed above, which uses it to compute a fluid temperature error.

It will be understood by those skilled in the art that other types of control loops may be used. For example, main controller 224 or heat exchanger controller 244 may utilize one or more PI loops, PD loops, and/or other types of control equations. In some embodiments, the coefficients used with the control loops may be varied by the controller 224 or 244 depending upon the patient's temperature reaction to the thermal therapy, among other factors. One example of such dynamic control loop coefficients is disclosed in commonly assigned U.S. patent application Ser. No. 62/577,772 filed on Oct. 27, 2017, by inventors Gregory Taylor et al. and entitled THERMAL SYSTEM WITH MEDICATION INTERACTION, the complete disclosure of which is incorporated herein by reference.

Regardless of the specific control loop utilized, main controller 224 or heat exchanger controller 244 implements the loop(s) multiple times a second in at least one embodiment, although it will be understood that this rate may be varied widely. After the controller 224 or 244 has output a heat/cool command to heat exchanger 206, the controller 224 or 244 takes another patient temperature reading (from sensor 252) and/or another fluid temperature reading (from sensor 222) and re-performs the loop(s). The specific loop(s)

used, as noted previously, depends upon whether thermal control unit 174 is operating in the manual mode or automatic mode.

It will also be understood by those skilled in the art that the output of any control loop used by thermal control unit 174 may be limited such that the temperature of the fluid delivered to thermal pads 178 never strays outside of a predefined maximum and a predefined minimum. Examples of such a predefined maximum temperature and predefined minimum temperature are disclosed and discussed in greater detail in commonly assigned U.S. patent application Ser. No. 16/222,004 filed Dec. 17, 2018, by inventors Gregory S. Taylor et al. and entitled THERMAL SYSTEM WITH GRAPHICAL USER INTERFACE, the complete disclosure of which is incorporated herein by reference. The predefined minimum temperature is designed as a safety temperature and may be set to about four degrees Celsius, although other temperatures may be selected. The predefined maximum temperature is also implemented as a safety measure and may be set to about forty degrees Celsius, although other values may be selected.

In some embodiments of thermal control unit 174, such as the embodiment shown in FIG. 6, thermal control unit 174 also includes a reservoir valve 254 that is adapted to selectively move fluid reservoir 184 into and out of line with circulation channel 202. Reservoir valve 254 is positioned in circulation channel 202 between air remover 234 and valve 236, although it will be understood that reservoir valve 254 may be moved to different locations within circulation channel 202. Reservoir valve 254 is coupled to circulation channel 202 as well as a reservoir channel 256. When reservoir valve 254 is open, fluid from air remover 234 flows along circulation channel 202 to pump 200 without passing through reservoir 184 and without any fluid flowing along reservoir channel 256. When reservoir valve 254 is closed, fluid coming from air remover 234 flows along reservoir channel 256, which feeds the fluid into reservoir 184. Fluid inside of reservoir 184 then flows back into circulation channel 202 via valve 236. Once back in circulation channel 202, the fluid flows to pump 200 and is pumped to the rest of circulation channel 202 and thermal pads 178 and/or bypass line 228. In some embodiments, reservoir valve 254 is either fully open or fully closed, while in other embodiments, reservoir valve 254 may be partially open or partially closed. In either case, reservoir valve 254 is under the control of main controller 224.

In those embodiments of thermal control unit 174 that include a reservoir valve, thermal control unit 174 may also include a reservoir temperature sensor 258. Reservoir temperature sensor 258 reports its temperature readings to main controller 224. When reservoir valve 254 is open, the fluid inside of reservoir 184 stays inside of reservoir 184 (after the initial drainage of the amount of fluid needed to fill circulation channel 202 and thermal pads 178). This residual fluid is substantially not affected by the temperature changes made to the fluid within circulation channel 202 as long as reservoir valve 254 remains open. This is because the residual fluid that remains inside of reservoir 184 after circulation channel 202 and thermal pads 178 have been filled does not pass through heat exchanger 206 and remains substantially thermally isolated from the circulating fluid. Two results flow from this: first, heat exchanger 206 does not need to expend energy on changing the temperature of the residual fluid in reservoir 184, and second, the temperature of the circulating fluid in circulation channel 202 will deviate from the temperature of the residual fluid as the circulating fluid circulates through heat exchanger 206.

In some embodiments, main controller 224 utilizes a temperature control algorithm to control reservoir valve 254 that, in some embodiments, is the same as the temperature control algorithm 160 disclosed in commonly assigned U.S. patent application Ser. No. 62/577,772 filed on Oct. 27, 2017, by inventors Gregory Taylor et al. and entitled THERMAL SYSTEM WITH MEDICATION INTERACTION, the complete disclosure of which is incorporated herein by reference. In other embodiments, main controller 224 utilizes a different control algorithm. In still other embodiments, thermal control unit 174 is modified to omit reservoir valve 254, reservoir channel 256, and reservoir temperature sensor 258. Thermal control unit 174 may also be modified such that reservoir 184 is always in the path of circulation channel 202. Still other modifications are possible.

It will be understood that the particular order of the components along circulation channel 202 of thermal control unit 174 may be varied from what is shown in FIG. 6. For example, although FIG. 6 depicts pump 200 as being upstream of heat exchanger 206 and air separator 234 as being upstream of pump 200, this order may be changed. Air separator 234, pump 200, heat exchanger 206 and reservoir 184 may be positioned at any suitable location along circulation channel 202. Indeed, in some embodiments, reservoir 184 is moved so as to be in line with and part of circulation channel 202, rather than external to circulation channel 202 as shown in FIG. 6, thereby forcing the circulating fluid to flow through reservoir 184 rather than around reservoir 184. Further details regarding the construction and operation of one embodiment of thermal control unit 174 that are not described herein may be found in commonly assigned U.S. patent application Ser. No. 14/282,383 filed May 20, 2014, by inventors Christopher Hopper et al. and entitled THERMAL CONTROL SYSTEM, the complete disclosure of which is incorporated herein by reference.

In some embodiments, thermal pads 178 are constructed in accordance with any of the thermal pads disclosed in any of the following commonly assigned U.S. patent applications: Ser. No. 15/675,061 filed Aug. 11, 2017, by inventors James Galer et al. and entitled THERMAL THERAPY DEVICES; Ser. No. 62/778,034 filed Dec. 11, 2018, by inventors Andrew M. Bentz et al. and entitled THERMAL SYSTEM WITH THERMAL PAD FILTERS; and Ser. No. 15/675,066 filed Aug. 11, 2017, by inventor James K. Galer and entitled THERMAL SYSTEM, the complete disclosures of all of which are incorporated herein by reference. Still other types of thermal pads 178 may be used with thermal control system 172, and thermal control unit 174 may be modified from its construction described herein in order to accommodate the particular thermal therapy pad(s) it is used with.

In those embodiments of thermal control unit 174 that include one or more location sensors 242, such location sensors 242 may take on a variety of different forms. For example, in one embodiment, thermal control unit 174 determines its location using any of the same methods and/or sensors disclosed for determining patient support apparatus location in commonly assigned U.S. Pat. No. 9,838,836 issued Dec. 5, 2017, to inventors Michael J. Hayes et al. and entitled PATIENT SUPPORT APPARATUS COMMUNICATION SYSTEMS, the complete disclosure of which is incorporated herein by reference. Still other automatic location detection methods may be used, including, but not limited to, the use of cellular network trilateration and/or Global Positioning System (GPS) sensors.

Gateway node 92*a* of thermal control unit 174, like gateway node 92 of patient support apparatus 20, includes one or more wired and/or wireless network transceivers (e.g. Ethernet port, USB port, ZigBee radio, and/or WiFi radio) adapted to communicate with both the local onboard network 248 (e.g. a CAN network, a LIN network, etc.) and the healthcare facility's local area network 124 and/or other electronic device(s) positioned off-board thermal control unit 174. Certain data that is received via gateway node 92*a* from the off-board network 124 is forwarded onto the local onboard network 248 and processed by one or more of the node(s) 224, 238, 244 to which such data pertains, and gateway node 92*a* is further adapted to transmit selected traffic on the local network 248 to one or more servers in communication with the healthcare facility's local area network 124 and/or to one or more other off-board electronic devices. The operation of gateway node 92*a* is discussed in greater detail below.

In some embodiments, gateway node 92*a* of thermal control unit 174 is configured to communicate with the same patient support apparatus server 120 (via a wireless access point 122) that patient support apparatus 20 is configured to communicate with. In other embodiments, gateway node 92*a* (and/or gateway node 92 of patient support apparatus 20) may be configured to communicate with a server that is hosted on the Internet, such as server 132, rather than the local area network 124. In other embodiments, gateway node 92*a* may be configured to communicate with still other servers, whether on local area network 124 and/or on the Internet. In some embodiments, gateway node 92*a* may be configured to communicate directly with gateway node 92 of patient support apparatus 20 so that patient support apparatus 20 and thermal control unit 174 can communicate with each other without using any of the healthcare facility's communication infrastructure (e.g. access points 122 and/or any other structures of local area network 124). The direct communication between patient support apparatus 20 and thermal control unit 174 may be bidirectional and, in some embodiments, may utilize a different communication protocol than the one gateways 92 and 92*a* use to communicate with wireless access point(s) 122. For example, the direct communication between patient support apparatus 20 and thermal control unit 174 may utilize Bluetooth communication, ZigBee communication, USB communication, and/or some other type of communication. In some embodiments, gateways 92 and/or 92*a* include a wired port, such as an Ethernet port, for communicating with local area network 124. In other embodiments, gateways 92 and/or 92*a* may include a WiFi radio, or other wireless transceiver, or communicating with local area network 124, and/or they may include both wireless and wired communication structures for communicating with network 124.

In some embodiments of thermal control unit 174 and/or patient support apparatus 20, gateway 92 and/or 92*a* is configured to send messages to one or more individuals in response to an alarm condition being detected. Once coupled to network 124, gateway 92 and/or 92*a* may be configured to send the alarm message in any conventional manner, including, but not limited to, sending the message to one or more servers on the local area network 124 that then forward the message to the appropriate mobile electronic device (e.g. smart phone, tablet, pager, laptop computer, etc.) of the corresponding nurse, clinician, or other user. Such servers include, but are not limited to, one or more commercially available paging, texting, emailing, and/or messaging servers.

Figure 7:
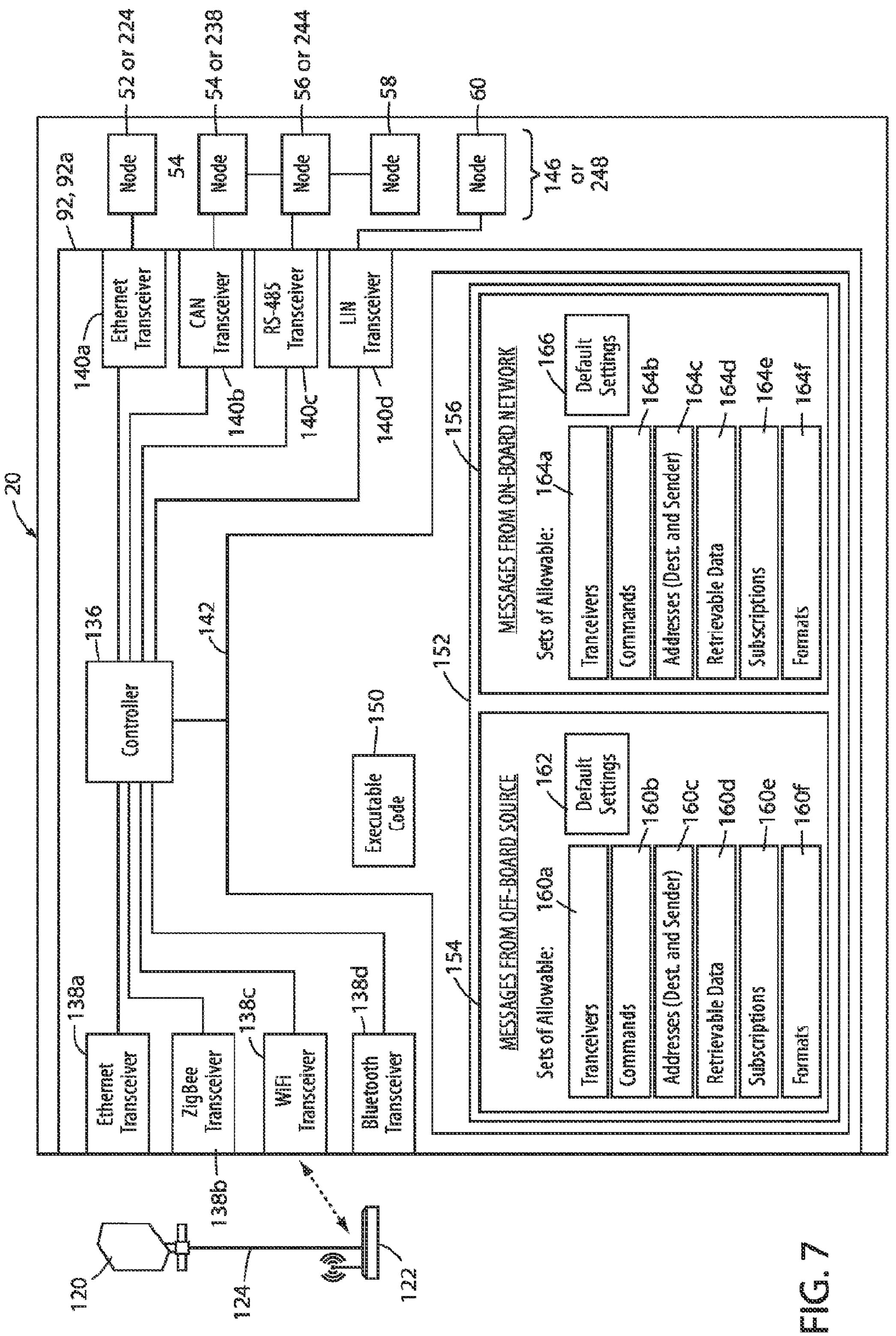
FIG. 7 is a block diagram of a gateway node that may be incorporated into the patient support apparatus of FIG. 1 and/or the thermal control unit of FIG. 4.

FIG. 7 illustrates in greater detail various internal components of gateway node 92 of patient support apparatus 20 and gateway node 92*a* of thermal control unit 174. In some embodiments, gateway node 92 and gateway node 92*a* are the same, other than a configuration file that is loaded onto the gateway node 92, as will be discussed in greater detail below. Indeed, in some embodiments, gateway node 92*a* can be originally supplied with a configuration file that is designed for thermal control unit 174, and then, if it is desired to switch node 92*a* to work with patient support apparatus 20, it can be supplied with a new configuration file designed for patient support apparatus 20, and gateway node 92*a* can then be switched to gateway node 92. The opposite is also true. If gateway node 92 is originally supplied with a configuration file that is designed for patient support apparatus 20, it can later be supplied with a new configuration file designed for thermal control unit 174, and gateway node 92 can then be switched to a gateway node 92*a*. These changes are all done without any changes to the hardware of the nodes 92, 92*a*. Indeed, in some embodiments, the executable file used in both nodes 92 and 92*a* is the same. It can therefore be seen that, in some embodiments, gateway nodes 92 and 92*a* are the same, other than the configuration file that is loaded onto them, and that they are therefore interchangeable with each other provided the correct configuration file is supplied to them.

The interchangeability of gateway nodes 92 and 92*a* applies not only to gateway nodes that are used on patient support apparatuses 20 and thermal control units 174, but also to gateway nodes that are used on different models of patient support apparatuses 20 and/or thermal control units 174. Thus, for example, if a first model of patient support apparatus 20 uses a first gateway node with a first set of communication requirements and a second patient support apparatus 20 uses a second gateway node with a second set of communication requirements, the first gateway node can be converted to the second gateway node, or vice versa, simply by loading a new configuration file into the gateway node. The gateway node 92 or 92*a* can therefore be dynamically modified to suit whichever medical device, or brand of medical device, it is desired to operate with without requiring any new executable file be uploaded to the gateway. Further details of gateway nodes 92 and 92*a* are provided below.

Gateway node 92, 92*a* includes a gateway controller 136, a plurality of off-board communication transceivers 138*a-d*, a plurality of onboard communication transceivers 140*a-d*, and a memory 142. In the particular embodiment illustrated in FIG. 7, there are four off-board communication transceivers 138*a-d*: an Ethernet transceiver 138*a*, a ZigBee transceiver 138*b*, a WiFi transceiver 138*c*, and a Bluetooth transceiver 138*d*. It will be understood that this may be modified substantially from what is shown in FIG. 7, both in terms of the number of off-board transceivers 138 and the specific types of off-board transceivers 138. Similarly, in the particular embodiment illustrated in FIG. 7, there are four onboard communication transceivers 140*a-d*: an Ethernet transceiver 140*a*, a Controller Area Network (CAN) transceiver 140*b*, an RS-485 transceiver 140*c*, and a Local Interconnect Network (LIN) transceiver 140*d*. As with the off-board transceivers 138*a-d*, the onboard transceivers 140*a-d* may also be modified substantially from what is shown in FIG. 7, both in terms of the number of transceivers and the specific types of onboard transceivers 140. Still further, it will be understood that both the number and the type of off-board transceivers 138 may be different from the number and type of onboard transceivers 140 used on gateway node 92.

Each transceiver 138, 140 is adapted to transmit and receive messages over an associated communication medium (e.g. wires, fiber optics, electromagnetic waves, etc.) according to the particular protocol of that particular transceiver. Thus, for example, WiFi transceiver 138*c* is adapted to transmit and receive WiFi messages from an off-board device, such as one or more conventional wireless access points 122. As such, transceiver 138*c* may use any of the various WiFi protocols (IEEE 802.11b, 801.11g, 802.11n, 802.11ac . . . , etc.). As another example, Ethernet transceivers 138*a* and/or 140*a* may include a standard RJ-45 jack, or the like, that is adapted to receive a standard network cable (e.g. CAT-6) and transmit and receive messages over that cable according to the conventional Ethernet protocol.

Onboard transceivers 140*a-d* of gateway node 92, 92*a* are shown coupled to one or more of the nodes of the particular medical device to which gateway node 92, 92*a* is a part of (e.g. nodes 52, 54, 56, 58, and/or 60 of patient support apparatus 20, nodes 224, 238, and 244 of thermal control unit 174). These nodes form a local, onboard network (146 or 248). It will be understood that the particular composition and structure of onboard network 146, 248 shown in FIG. 7, including the specific connections between the nodes and/or the connections between one or more of those nodes and the transceivers 140, may vary significantly from what is shown in FIG. 7. That is, for example, in some embodiments, patient support apparatus 20 and/or thermal control unit 174 may include an onboard network 146, 248 having fewer or greater numbers of nodes, and the onboard network 146, 248 may include only a single connection to one of the transceivers 140. As another alternative, patient support apparatus 20 and/or thermal control unit 174 may include multiple onboard networks 146, 248 with different nodes coupled thereto, and each network may be communicatively coupled to gateway node 92, 92*a* via different onboard transceivers 140*a-d*. In sum, the particular set of connections between the nodes and transceivers 140*a-d* shown in FIG. 7 is but one illustrative manner of organizing network 146, 248 and its connections to gateway node 92, 92*a* amongst many that may be utilized in accordance with the principles of the present disclosure.

Off-board transceivers 138*a-d* are not shown coupled to any off-board network or devices in FIG. 7 other than WiFi transceiver 138*c*, which is shown communicatively coupled to an access point 122 of the healthcare facility's computer network 124. It will be understood that this is merely representative of one type of communication set up for gateway node 92, 92*a*. Thus, for example, Bluetooth transceiver 138*d* may be communicatively coupled to one or more Bluetooth devices that are positioned within range of patient support apparatus 20 or thermal control unit 174, such as, but not limited to, smart phones, tablet computers, portable computers, or other Bluetooth-enabled devices. Similarly, ZigBee transceiver may be communicatively coupled to one or more ZigBee enabled devices that are positioned within range of patient support apparatus 20 and/or thermal control unit 174. Ethernet transceiver 138*a* is intended to connect via a cable with another computer and/or another computer network (e.g. network 126). As was noted previously, the set of transceivers 138*a-d* shown in FIG. 7 may be varied for different embodiments of gateway node 92, 92*a* including fewer transceivers 138 or a greater number of transceivers. When more transceivers 138 are included, such additional transceivers may include a Universal Serial Bus (USB) transceiver and/or another type of transceiver.

In some embodiments, one or more of the transceivers 138*a-d* and/or 140*a-d* may be partially or wholly built into main controller 136 (i.e. main controller 136 may include one or more microcontrollers that include a set of pins that output messages in the particular format of the transceiver (e.g. CAN format)). In other embodiments, transceivers 138, 140 may be components physically separate from the one or more microcontrollers of main controller 136. Each transceiver 138, 140 formats the messages and/or commands it sends into the packet format, frame format, or other format of the communication protocol that it uses for its communications, and, as appropriate, establishes the correct voltage levels on the correct wires (if wired communication). Similarly, each transceiver 138, 140 also receives packets, frames, or other data structures from the other devices or node and extracts the contents of those packets, frames, or other data for processing by gateway controller 136. The transceivers 138, 140 may also handle the arbitration and other tasks associated with the first and second layers of the OSI communication model.

Gateway node 92, 92*a* is configured to manage the communication exchange between off-board devices (including network 124) and onboard network 146 or 248. More particularly, gateway node 92, 92*a* is configured to manage and control what information from onboard network 146, 248 is transmitted off-board the medical device (patient support apparatus 20 or thermal control unit 174), as well as to control what information that is received from a source off-board the medical device is transmitted to onboard network 146, 248. In addition to controlling the content of the onboard information that is transmitted off-board, and vice versa, gateway node 92, 92*a* is configured to control when such information is transmitted, the format of the transmitted information, the destination to which such information is transmitted, which one of the transceivers 138, 140 is to be used for transmitting such information, and how the information from the one or more off-board sources is to be processed onboard and responded to, if at all.

In order to carry out this management of the onboard/off-board information exchange, controller 136 of gateway node 92, 92*a* includes one or more microcontrollers adapted to execute an executable code 150 stored in memory 142 of gateway node 92, 92*a*. The executable code 150 is executed by the controller 136 upon power up. That is, when power is applied to controller 136, it initially executes a boot loader, or the like, that instructs the controller 136 to begin executing code 150 (or alternatively instructs controller 136 to load an operating system that then begins executing code 150). However started, code 150, in turn, instructs controller 136 to read and utilize a configuration file 152 during the performance of its functions. Because configuration file 152 is not an executable set of instructions, but instead is a file, it can be replaced and/or updated while controller 136 is executing executable code 150 without requiring controller 136 to stop the performance of executable code 150. In other words, because executable code 150 includes instructions to read from configuration file 152 and, in some cases, to replace configuration file 152 with a new configuration file 152, controller 136 is able to make a variety of adjustments to the capabilities of gateway node 92, 92*a* without having to reboot controller 136 and/or without having to cycle power on and off for controller 136. The adjustments that can be made to the capabilities of gateway node 92, 92*a* by replacing and/or updating configuration file 152 are described in more detail below.

As shown in FIG. 7, configuration file 152 includes a set of off-board settings 154 and a set of onboard settings 156. Off-board settings are used by controller 136 in the processing of data received from and/or transmitted to one or more devices that are positioned off-board the medical device (e.g.

patient support apparatus 20 or thermal control unit 174), such as, but not limited to, server 120. Onboard settings are used by controller 136 in the processing of data received from and/or transmitted to onboard network 146 or 248. Off-board settings 154 includes a set of allowable parameters 160*a-f* and a set of default settings 162 for those parameters. Onboard settings 156 include a set of allowable parameters 164*a-f* and a set of default settings 166 for those parameters. As will be discussed in greater detail below, these various components of configuration file 152 determine the limits and functionality of gateway node 92, 92*a* with respect to what off-board messages are to be passed onto the onboard network 146 or 248 (and how), what onboard messages are to be passed off-board the medical device (and how), and what messages are to be processed by gateway node 92, 92*a* itself (and how).

With respect to the allowable set of parameters 160*a-f* contained within off-board settings 154, these parameters dictate what messages can be received from off-board the medical device by gateway node 92, 92*a*, what content the messages may have, what formatting the messages may have, what transceivers 138*a-d* the inbound messages may be received from, what transceivers 138*a-d* the outbound messages are able to be transmitted through, what addresses the outbound messages may be received from, and what addresses the inbound messages should be addressed to. These concepts are described in more detail below with respect to each individual set of allowable parameters.

Turning first to the set of allowable transceivers 160*a*, this set of parameters informs gateway controller 136 of the transceivers 138*a-d* that are available for use with respect to incoming messages from off-board device(s), as well as what transceivers are available for use for sending outbound messages to off-board device(s). The data contained within set 160*a* may dictate what transceivers are available at a universal level, or it may dictate what transceivers are available on an individualized and/or contingent level. With respect to the former, the data may universally dictate, for example, that all outbound messages can only be sent via WiFi transceiver 138*c*, and/or that all inbound messages can only be received via WiFi transceiver 138*c* (in which case messages received on the other transceivers 138*a, b*, and *d* are ignored). Other transceivers 138*c* can, of course, be designated within parameters set 160*a* as being universally available for use.

With respect to more individualized data, parameter set 160*a* may specify that certain types of messages are able to be sent via specific transceivers 138*a-d*, and/or that certain types of messages are able to be received over specific ones of the transceivers 138*a-d*. The instructions as to which transceiver 138 is available for use for which messages may be based upon the content of the message(s), the destination of the message, the source of the message, the format of the message, the authorization level associated with the message, the time at which the message is to be sent or was received at, and/or other factors. Thus, when gateway node 92, 92*a* consults configuration file 152 during its operation, it may determine, for example, that technical data regarding the operation of the medical device (e.g. patient support apparatus 20 or thermal control unit 174), such as motor current draw, errors, usage statistics, settings, etc., is able to be transferred off-board the medical device via both WiFi transceiver 138*c* and Bluetooth transceiver 138*d*, while status data (e.g. position of the siderails 34, brake status, height of litter frame 28, current temperature of the fluid delivered to thermal pads 178—measured by outlet temperature sensor 222, rate of heat transfer to/from the circulating fluid, etc.) and patient data (e.g. patient weight, fall risk, bed sore risk, current patient temperature measured by probe 252, etc.) are only able to be transferred off-board the medical device via WiFi transceiver 138*c*. Numerous other types of combinations, permutations, and variations of the transceiver parameters 160*a* are possible.

It should be noted that the transceiver parameters 160*a* do not necessarily dictate which transceivers 138*a-d* are to be used for any particular message, but instead define which transceivers 138*a-d* are available for use by gateway node 92, 92*a*. That is, it is a list of permitted transceivers, not necessarily a list of commanded transceivers. As will be discussed in more detail below, the default settings 162 include one or more commands that dictate what transceiver(s) 138 are to be used, either universally or in specific situations. Still further, these default settings may be updated and changed without installing a new configuration file 152, provided that the initial configuration file 152 includes within its command parameters 160*b* the ability to receive commands for changing these default settings, as will also be discussed in more detail below.

In addition to the transceiver parameters 160*a*, configuration file 152 also includes a set of allowable command parameters 160*b* (FIG. 7). The command parameters 160*b* define what commands gateway node 92 is able to implement based on messages received through one of the off-board transceivers 138*a-d*. Thus, if gateway node 92 receives a message from patient support apparatus server 120 via WiFi transceiver 138*c* and that message is a command for gateway node 92, 92*a* to, for example, replace configuration file 152 with a new configuration file, gateway controller 136 will first consult the current configuration file 152 (not the new one) to see if such a command is an acceptable command or not. In other words, it will check command parameters 160*b* to see if replacing the configuration file 152 with a new configuration file is an acceptable command or not. In the embodiments discussed herein, this type of replacement command will be included within command parameters 160*b* such that gateway node 92, 92*a* will respond to such a replacement command by replacing configuration file 152 with a new configuration file.

If gateway node 92, 92*a* receives a command from an off-board source (e.g. patient support apparatus server 120) that is not contained within the allowable command parameters 160*b*, it will not implement that command. It is therefore possible to easily change what commands patient support apparatus 20 and/or thermal control unit 174 is responsive to by simply replacing its existing configuration file 152 with a new configuration file that includes a new set of allowable command parameters 160*b*. This enables the manufacturer of patient support apparatus 20 and/or thermal control unit 174 to more easily customize the functionality of patient support apparatus 20 and/or thermal control unit 174 for different customers, as well as to modify the functionality of the patient support apparatus 20 and/or thermal control unit 174 for the same customers when their needs change.

For example, if patient support apparatus 20 initially includes a configuration file that does not include within command parameters 160*b* a command for remotely arming the exit detection system onboard patient support apparatus 20, any commands sent from an off-board source to patient support apparatus 20 instructing it to arm its exit detection system will not be implemented. However, if a customer wishes to be able to remotely arm the exit detection system of the patient support apparatus, this can be easily accomplished by sending a command to gateway node 92 instructing it to replace its current configuration file 152 with a new configuration file 152 that includes within the allowable command parameters 160*b* the command for remotely arming the exit detection system. The new configuration file may be one that is preloaded into the memory of patient support apparatus 20, or it may be transferred to patient support apparatus 20 from an acceptable off-board source via one or more of the transceivers 138*a-d* (subject to any limitations on the transceivers contained within the existing transceiver parameters 160*a*).

Similar modifications can be made for gateway node 92*a* of thermal control unit 174. For example, if thermal control unit 174 initially includes a configuration file that does not include within command parameters 160*b* a command for remotely activating a particular alarm function of the thermal control unit 174, any commands sent from an off-board source to thermal control unit 174 instructing it to activate that particular alarm function not be implemented. However, if a customer wishes to be able to remotely activate that particular alarm function (e.g. an alarm when a flow of the fluid through one of the thermal pads 178 decreases below a threshold), this can be easily accomplished by sending a command to gateway node 92*a* instructing it to replace its current configuration file 152 with a new configuration file 152 that includes within the allowable command parameters 160*b* the command for remotely activating that particular alarm. The new configuration file may be one that is preloaded into the memory of thermal control unit 174, or it may be transferred to thermal control unit 174 from an acceptable off-board source via one or more of the transceivers 138*a-d* (subject to any limitations on the transceivers contained within the existing transceiver parameters 160*a*).

Modifications to the functionality of the medical device that contains gateway node 92, 92*a* can therefore be made after the medical device has been manufactured and installed in a healthcare facility. Further, these modifications can be made while the medical device is operating and without interrupting the operation of the medical device.

The command parameters 160*b* of configuration file 152 (FIG. 7) may be used, either alone or in combination with one or more of the other parameters 160*a, c-f*, to improve the security of patient support apparatus 20 and/or thermal control unit 174. That is, if an unauthorized source gains access to local network 146 and attempts to export data from patient support apparatus 20 and/or thermal control unit 174 by sending one or more read commands, gateway node 92, 92*a* can help to prevent such unauthorized data reading if configuration file 152 is defined such that the commands sent from the unauthorized device are not acceptable commands (i.e. not contained within command parameters 160*b*). Thus, for example, if the unauthorized party sends a command to gateway node 92, 92*a* commanding it to read and export the name of the patient currently assigned to patient support apparatus 20 and/or thermal control unit 174 (which may be stored in the memory of one of the nodes of onboard network 146 or 248), configuration file 152 may be defined such that patient name data (or any other desired data) cannot be exported by gateway node 92, 92*a*. This prohibition against the export of certain data may be universal—that is, it may apply to any device that attempts to read this data—or it may be more specific, such that is only applies to read commands that are received from off-board sources without established security credentials (such as, but not limited to, sources that do not have an authorized address, as discussed in more detail below with respect to address parameters 160*c*).

The command parameters 160*b* of configuration file 152 may be used for still other purposes, including implementing a wide variety of improvements to patient support apparatus 20 and/or thermal control unit 174 that can be made for increasing customer satisfaction. For example, if a healthcare facility purchases a set of patient support apparatuses 20 that have motorized actuators 84 that can only be activated in response to physically touching one or more controls on control panels 48, and the healthcare facility later wants to allow its caregiver employees to be able to activate one or more of those actuators 84 without having to touch any control panel 48, the modification of configuration file 152 can be used to implement this change. For example, if the healthcare facility wants its caregivers to be able to use their individual smart phones to be able to activate (and deactivate) motorized actuators 84, a new configuration file 152 can be downloaded that includes a new set of allowable command parameters 160*b* wherein that new set allows for off-board control of actuators 84. In some situations, the new configuration file 152 may include a new set of transceiver parameters 160*a* that allows such commands to be received through Bluetooth transceiver 138*d*, thereby allowing the caregivers to use their smart phones to control the actuators 84 of patient support apparatus 20 using the built-in Bluetooth functionality of their smart phones.

As another example, if a healthcare facility purchases a set of thermal control units 174 that have one or more parameters that can only be changed locally at the thermal control unit 174 (e.g. in response to physically touching one or more controls on control panel 194, and the healthcare facility later wants to allow its caregiver employees to be able to change one or more of these parameters remotely (i.e. without having to touch any controls one control panel 194), the modification of configuration file 152 can be used to implement this change. For example, if the healthcare facility wants its caregivers to be able to use their individual smart phones to be able to set a desired patient temperature, or to change a mode of operation (manual or automatic), or to stop receiving (or start receiving) certain kinds of alerts on their smart phones, etc. a new configuration file 152 can be downloaded that includes a new set of allowable command parameters 160*b* wherein that new set allows for these types of changes to be made via an off-board command. In some situations, the new configuration file 152 may include a new set of transceiver parameters 160*a* that allows such commands to be received through Bluetooth transceiver 138*d*, thereby allowing the caregivers to use their smart phones to control these parameters using the built-in Bluetooth functionality of their smart phones. Alternatively, or additionally, the commands may be received through WiFi transceiver 138*c*, which could also, or alternatively, allow the caregivers to use their smart phones to control these parameters using the built-in WiFi functionality of their smart phones.

It will be of course understood that the aforementioned examples of modifying command parameters 160*b* of configuration file 152 to enable caregivers to remotely activate actuators 84 and/or remotely change parameters of thermal control unit 174 using their smart phones are but two of many examples of the types of improvements in the functionality of patient support apparatus 20 and/or thermal control unit 174 that can be implemented. Some additional examples include modifying command parameters 160*b* to allow the mobile phones (or other portable electronic devices) of the caregivers to activate and deactivate other functions of patient support apparatus 20 and/or thermal control unit 174 (e.g. activating/deactivating a brake, arming/disarming a monitoring system, deactivating an alert, activating the scale to take a weight readings, forwarding information from patient support apparatus 20 to an EMR server, controlling a mattress therapy function, changing the mode of operation of thermal control unit 174, changing a temperature setting, pausing/starting a thermal therapy session, and still others); to allow the caregiver's mobile devices to read data from patient support apparatus 20 and/or thermal control unit 174 (such as, but not limited to, the patient's weight and/or temperature); and/or to allow the caregiver's mobile devices to enter data that is stored onboard patient support apparatus 20 and/or thermal control unit 174 (e.g. the patient's name, assigned caregiver, etc.).

Similar types of modifications can also or alternatively be made with respect to devices other than the caregiver's mobile electronic devices (e.g. smart phones, tablet computers, laptops, etc.). For example, any of the aforementioned modifications to the allowable command parameters 160*b* may be made to enable the mobile electronic devices of, as appropriate, patients, visitors, technicians, cleaning staff, biomedical engineers, maintenance personnel, etc. to remotely activate or deactivate one or more features of patient support apparatus 20 and/or thermal control unit 174, to remotely read one or more types of data from patient support apparatus 20 and/or thermal control unit 174, and/or to remotely write data to one or more nodes of onboard network 146 and/or 248.

As yet another example, modifications to command parameters 160*b* (FIG. 7) may also or alternatively be made to enable patient support apparatus 20 and/or thermal control unit 174 to communicate with one or more medical devices that it was not previously able to communicate with. For example, if a thermal control unit 174 is being used with a patient while the patient is resting on patient support apparatus 20, a modified set of allowable command parameters 160*b* may be implemented that allow gateway node 92 of patient support apparatus 20 to, for example, send the patient's weight and/or patient's movement patterns directly to the thermal control unit 174 via one or more of the transceivers 138. Alternatively, or additionally, a modified set of allowable command parameters 160*b* may be implemented that allow gateway node 92*a* of thermal control unit 174 to send the patient's temperature and/or other parameters directly to patient support apparatus 20 via one or more of the transceivers 138.

In some embodiments, thermal control unit 174 may be constructed to include any of the features and/or functions disclosed in the thermal control units disclosed in any of the following commonly assigned patent applications: U.S. patent application Ser. No. 14/282,383 filed May 20, 2014, by inventors Christopher Hopper et al. and entitled THERMAL CONTROL SYSTEM; U.S. patent application Ser. No. 15/616,574 filed Jun. 7, 2017, by inventors Gregory S. Taylor et al. and entitled THERMAL CONTROL SYSTEM; U.S. patent application Ser. No. 15/880,721 filed Jan. 26, 2018, by inventors Erika Fojtik et al. and entitled THERMAL CONTROL SYSTEM WITH FLUID CARTRIDGES; U.S. patent application Ser. No. 15/936,860 filed Mar. 27, 2018, by inventors Gregory S. Taylor et al. and entitled THERMAL SYSTEM; and U.S. patent application Ser. No. 16/218,883 filed Dec. 13, 2018, by inventors Gregory S. Taylor et al. and entitled THERMAL SYSTEM WITH OVERSHOOT REDUCTION, the complete disclosures of all of which are incorporated herein by reference. Of course, other types of modifications may be made to the set of allowable command parameters 160*b* for allowing patient support apparatus 20 and/or thermal control unit 174 to communicate with other types of medical devices, such as, but not limited to, ventilators, DVT pumps, IV controllers, respirators, vital sign monitors, blood sensors (e.g. glucose monitors, oxygenation sensors, etc.), and/or other still other types of medical devices.

Modifications to the command parameters 160*b* may also be utilized to allow one or more physically separate medical devices to utilize some or all of the screen space of the one or more displays 90 positioned onboard patient support apparatus 20 and/or the display 198 of thermal control unit 174. In such embodiments, the one or more medical devices may display on displays 90 and/or 198 one or more controls that, when activated, cause the medical device to take one or more actions. In effect, such embodiments allow the one or more medical devices, which are separate structures from patient support apparatus 20 and thermal control unit 174, to utilize one or more control panels of patient support apparatus 20 and/or thermal control unit 174 for controlling the one or more medical devices. In other words, the control panels of patient support apparatus 20 and/or thermal control unit 174 can be temporarily (or permanently) modified to enable the control of one or more separate medical devices. Further details regarding this type of screen space sharing are provided in commonly assigned U.S. patent application Ser. No. 15/996,037 filed Jun. 1, 2018, by inventors Krishna Bhimavarapu et al. and entitled PATIENT CARE DEVICES WITH OPEN COMMUNICATION, the complete disclosure of which is incorporated herein by reference.

Modifications to command parameters 160*b* (FIG. 7) may also be used to allow gateway node 92 to accommodate hardware changes made onboard patient support apparatus 20 and/or thermal control unit 174. For example, if a patient support apparatus 20 that doesn't include a propulsion system (and therefore doesn't include propulsion node 60) is subsequently modified to include such a propulsion system, commands for controlling the propulsion system and/or reading data or setting data regarding the propulsion system can be processed through gateway node 92 without having to rewrite any of the executable code followed by gateway node 92. Thus, if the patient support apparatus 20 initially includes no propulsion system and its command parameters 60*b* do not include a command for transmitting data about a propulsion system to an off-board source, the addition of a new configuration file after a propulsion system is installed on patient support apparatus 20 can easily allow the off-board source to be able to receive data regarding the propulsion system. The new configuration file 152 merely has to add to the set of acceptable command parameters 160*b* a read command that reads data from the newly installed propulsion node 60 and transfers it to an off-board device (e.g. server 120). Similar modifications can be made, of course, to the configuration file 152 to accommodate other hardware modifications of patient support apparatus 20 besides the addition of a propulsion system.

With respect to thermal control unit 174, one example of new hardware changes that can be accommodated include the addition of auxiliary ports 192. Some embodiments of thermal control units 174 do not include auxiliary ports 192. However, if these embodiments are modified to include one or more auxiliary ports 192, which may receive data from one or more additional sensors (besides patient temperature probes 252), commands for using the data from these additional sensors can be processed through gateway node 92*a* without having to rewrite any of the executable code followed by gateway node 92*a*. Thus, if thermal control unit 174 initially includes no auxiliary ports 192 and its command parameters 60*b* do not include a command for transmitting data about from sensor coupled to an auxiliary port

192 to an off-board source, the addition of a new configuration file after an auxiliary port 192 has been installed on thermal control unit 174 can easily allow the off-board source to be able to receive data regarding the auxiliary sensor coupled to port 192. The new configuration file 152 merely has to add to the set of acceptable command parameters 160*b* a read command that reads data from the newly installed auxiliary port 192 and transfers it to an off-board device (e.g. server 120). Similar modifications can be made, of course, to the configuration file 152 to accommodate other hardware modifications of thermal control unit 174 besides the addition of one or more auxiliary ports 192.

As with the transceiver parameters 160*a*, the command parameters 160*b* may dictate what commands are allowed at a universal level, or they may dictate what commands are allowed on an individualized and/or contingent level. With respect to the former, the data may universally dictate, for example, that all commands to read data from the scale system onboard patient support apparatus 20 (or all commands to read a temperature from sensor 222 of thermal control unit 174) and report them to an off-board device are to be followed. With respect to the latter, the command parameter data 160 may be individualized such that the command to read scale data (or temperature data), for example, is only allowable if it is received from a particular address, if it is received at a particular time, if it is received from a particular transceiver 138, and/or if patient support apparatus 20 has a particular type of scale system onboard (and/or if thermal control unit 174 has a particular type of temperature sensor 222).

As is also similar to the transceiver parameters 160*a*, the command parameters 160*b* do not necessarily dictate which commands are to be implemented by gateway node 92, 92*a*, but instead merely define which commands are able to be implemented by gateway node 92, 92*a*. That is, it is a list of permitted commands, not necessarily a list of actual commands. As will be discussed in more detail below, the default settings 162 includes one or more functions that gateway node 92, 92*a* executes, along with the instructions for following any allowable command that it receives from either an off-board source or from onboard network 146 or 248.

In addition to the transceiver parameters 160*a* and command parameters 160*b*, configuration file 152 also includes a set of allowable addresses 160*c* (FIG. 7). The address parameters 160*c* define what addresses gateway node 92, 92*a* is able to use and accept with respect to both inbound and outbound messages that pass through, or are intended to pass through, one or more of the off-board transceivers 138*a-d*. Thus, if gateway node 92, 92*a* receives a message from patient support apparatus server 120 via WiFi transceiver 138*c* and that message has a source address, gateway controller 136 will consult the set of allowable address parameters 160*c* in the current configuration file 152 to see if the message has come from an acceptable address or not. If it has, it will process the message accordingly. If not, it will not process the message. Additionally, if the message includes a destination address for a particular node of onboard network 146, gateway controller 136 will also consult the allowable set of address parameters 160*c* in the current configuration file 152 to see if the node address in the message is an acceptable destination address. If it is, it will forward the message to the node with that address (provided such forwarding is not disallowed by any of the other parameters 160*a-b, d-f*). If it is not, it will not forward the message.

It will be understood that address parameters 160*c* may not only specify individual addresses, such as IP addresses or other types of addresses, but they may also include additional routing and/or access information, such as, but not limited to, one or more allowable Service Set Identifiers (SSID) for the healthcare computer network 124 (or other networks patient support apparatus 20 may be in communication with), a password for accessing the network 124 (or other network(s)), other authentication data for ensuring data security, a Transmission Control Protocol (TCP) port number for communicating with server 120 (or another server), etc.

As with the transceiver parameters 160*a* and the command parameters 160*b*, the address parameters 160*c* may dictate what addresses are allowed at a universal level, or they may dictate what addresses are allowed on an individualized and/or contingent level. With respect to the former, the data may universally dictate, for example, that a set of destination or source addresses are acceptable for all or a subset of messages. With respect to the latter, the address parameter data 160*c* may be individualized such that only certain addresses (destination and/or source) are acceptable for certain types of messages, that other addresses are not acceptable for any messages, and/or that still other addresses are only acceptable for still other types of messages.

As is also similar to the transceiver parameters 160*a* and the command parameters 160*b*, the address parameters 160*c* do not dictate what addresses are to be used by gateway node 92, 92*a* for any particular messages, but instead merely define which addresses are acceptable for gateway node 92, 92*a*. That is, it is a list of permitted addresses, not necessarily a list of commanded addresses. As will be discussed in more detail below, the default settings 162 includes one or more addresses that gateway node 92, 92*a* utilizes when carrying out acceptable commands and/or when carrying out its other functions.

In addition to the transceiver parameters 160*a*, command parameters 160*b*, and address parameters 160*c*, configuration file 152 also includes a set of allowable retrievable data parameters 160*d* (FIG. 7). The retrievable data parameters 160*d* define what data gateway node 92, 92*a* is able to retrieve from onboard network 146 or 248 and then use and/or transmit off-board patient support apparatus 20 or thermal control unit 174. Thus, if gateway node 92, 92*a* receives a message from patient support apparatus server 120 via WiFi transceiver 138*c* and that message requests, for example, the charge level of battery 78 or the flow rate through a first outlet port 186, gateway controller 136 will consult the set of allowable retrievable data 160*d* in the current configuration file 152 to see if the battery charge level and/or flow rate is data that can be transmitted off of patient support apparatus 20 or thermal control unit 174. If it is able to be transmitted, it will either read the messages onboard network 146 that indicate the battery charge level (or the messages onboard network 148 that indicate the flow rate through the port 186), or it will send a request to main control node 52 (or 224) requesting the current charge level of the battery 78 (or current flow rate data), and then, when that data is received, it will process it accordingly (e.g. transmit it to an off-board device). If it is not, it will not retrieve the battery status data or flow rate data and will not process the message.

As with the previously discussed parameters 160*a-c*, the retrievable data parameters 160*d* may dictate what data is retrievable at a universal level, or they may dictate what data is retrievable on an individualized and/or contingent level. With respect to the former, the data may universally dictate, for example, that all scale data and/or that all flow rate data is retrievable. With respect to the latter, the retrievable data parameter 160*d* may be individualized such that only certain data is retrievable by, say, caregivers with mobile phones that are able to communicate with one or more of the transceivers 138*a-d*, and that other data is only retrievable by server 120. The set of retrievable data parameters 160*d* can therefore be utilized to control who and/or what device has access to different data that is present on patient support apparatus 20 and/or thermal control unit 174.

As with the other allowable parameters 160*a-c, e-f*, the retrievable data parameters 160*d* may be combined with other parameters 160 to control what data is sent off of patient support apparatus 20 and/or thermal control unit 174 to one or more off-board devices. Thus, for example, when combined with address parameters 160*c*, configuration file 152 might dictate via retrievable data parameters 160*d* that only technicians are able to retrieve a first set of data from patient support apparatus 20 or thermal control unit 174 (via gateway node 92 or 92*a*, respectively), that only caregivers are able to retrieve a second set of data, that only server 120 is able to retrieve a third set of data, and/or that only remote server 132 is able to retrieve a fourth set of data. The first, second, third, and fourth sets of data may be mutually exclusive to each other, or they may overlap, either partially or wholly, with one or more of the other sets.

Similar to the other allowable parameters 160*a-c, e-f*, the retrievable data parameters 160*d* do not dictate what data is actually retrieved by gateway node 92, 92*a* in response to a particular message, but instead merely define which data it is possible for gateway node 92, 92*a* to retrieve. That is, it is a list of permitted data, not a command to retrieve particular data. As will be discussed in more detail below, the default settings 162 may contain one or more sets of data that the gateway node 92, 92*a* is instructed, by default, to retrieve and share with one or more off-board devices.

In addition to the parameters 160*a-d*, configuration file 152 also includes a set of allowable subscription parameters 160*e* (FIG. 7). The subscription parameters 160*e* define what types of subscriptions an off-board device may set up with respect to patient support apparatus 20 or thermal control unit 174. Thus, for example, an off-board device such as server 120 may subscribe to all exit alerts that are issued by patient support apparatus 20 and/or to all alarms that are issued by thermal control unit 174. The server may also subscribe to data regarding the status of the patient support apparatus's brake, siderails, height of litter frame 28, exit detection system status, etc., and/or it may subscribe to all data regarding the current patient's temperature, the current temperature of fluid delivered to the patient, and/or the amount of heat being withdrawn from, and/or added to, the patient by thermal control unit 174. These subscriptions may take on different forms, depending upon the content of allowable subscription parameters 160*e*. Thus, in one example, allowable subscription parameters 160*e* may allow an off-board device to set up a subscription to data that specifies that the data is only to be sent when it changes, or that it is to be sent only when it exceeds a threshold, or only when it falls below a threshold, or only when it changes by more than a threshold, or only at certain times, and/or to specify when and/or how frequently the data is to be sent off-board (e.g. continuously, intermittently every second, intermittently every minute, only at certain times, etc.).

As a result, when an off-board device requests to subscribe to certain data from patient support apparatus 20 or thermal control unit 174, gateway controller 136 will check to see if the subscription request is an allowable subscription request or not based upon the set of allowable subscription parameters 160*e*. If the requested subscription meets these parameters 160*e*, controller 136 will set up the subscription such that the subscribed data will be sent to the off-board device in the manner prescribed by the subscription. On the other hand, if the requested subscription does not meet the parameters 160, controller 136 will not set up the subscription and the off-board device will not get subscribed to the data it requested in the subscription request.

As with the other allowable parameters 160*a-d*, and *f*, subscription parameters 160*e* may be combined with one or more of the other parameters 160 in a particular configuration file 152. Thus, for example, retrievable data parameter 160*d* and subscription parameters 160*e* may be defined such that only certain types of data are retrievable for one or more subscriptions. As another example, the subscription parameters 160*e* may be combined with the address parameters 160*c* and/or the transceiver parameters 160*a* such that only devices with certain addresses, or only devices that utilize a particular transceiver 138, may subscribe to certain data. Still other combinations of parameters 160 may be implemented in a particular configuration file.

The allowable subscription data parameters 160*e* may dictate what types of subscriptions may be established at a universal level, or they may dictate what types of subscriptions may be established at an individualized and/or contingent level. With respect to the former, the subscription data 160*e* may universally dictate, for example, that the patient support apparatus or thermal control unit data is all subscribable with the same limitations. Alternatively, the subscription parameters 160*e* may be individualized such that only a first set of patient support apparatus data or thermal control unit data is subscribable in a first manner and/or by certain devices and/or at certain times, and that a second set of patient support apparatus data or thermal control unit data is subscribable in a second manner and/or by a different set of devices and/or at a different times. Still other variations in what data is subscribable and in what forms are possible.

Similar to the other allowable parameters 160*a-d, f*, the allowable subscription data 160*e* does not establish any subscriptions, but instead merely defines what types of subscriptions are possible (e.g. when data is reported off-board, to what it is reported, how it is reported, etc.). That is, it is a list of permitted subscriptions, not a command to establish any subscriptions. As will be discussed in more detail below, the default settings 162 may contain one or more subscriptions that the gateway node 92, 92*a* is instructed, by default, to fulfill with respect to one or more off-board devices.

It will be understood that the subscriptions referred to with respect to parameters 160*e* are subscriptions that one or more off-board devices set up with gateway node 92 to receive patient support apparatus 20 data, or with gateway node 92*a* to receive thermal control unit 174 data. These subscriptions are different from subscriptions that gateway node 92, 92*a* may establish with respect to one or more of the nodes 52-62 onboard patient support apparatus 20 or nodes 224, 238, and 244 onboard thermal control unit 174. Thus, onboard subscriptions may be set up by gateway node 92, 92*a*, for example, in response to a subscription that an off-board device has for a particular piece of data from patient support apparatus 20 or thermal control unit 174. For example, suppose server 120 sets up a subscription with gateway node 92 to receive periodic updates of the weight readings from load cells 80 onboard patient support apparatus 20. In order to fulfill this subscription, gateway node 92 may send a subscription request to main control node 52 requesting that gateway node 92 receive periodic updates of the load cell 80 readings. In response, when main control node 52 reports these periodic updates on network 146, gateway node 92 will read these updates and use them to fulfill the subscription that server 120 set up with gateway node 92. Alternatively, suppose server 120 sets up a subscription with gateway node 92*a* to receive periodic updates of the patient's temperature readings from patient temperature probe 252 onboard thermal control unit 174. In order to fulfill this subscription, gateway node 92*a* may send a subscription request to main controller node 224 requesting that gateway node 92*a* receive periodic updates of the readings from patient temperature probe 252. In response, when main controller node 224 reports these periodic updates on network 248, gateway node 92*a* will read these updates and use them to fulfill the subscription that server 120 set up with gateway node 92*a*.

In addition to the parameters 160*a-e*, configuration file 152 also includes a set of allowable format parameters 160*f* (FIG. 7). The format parameters 160*f* define what message formats are acceptable for communicating with one or more off-board devices. Thus, for example, gateway node 92, 92*a* may be configured via configuration file 152 to communicate with server 120 via the Simple Object Access Protocol (SOAP) or via the JavaScript Object Notation (JSON), or via some other format, service, and/or protocol.

As with the other allowable parameters 160*a-e*, format parameters 160*f* may be combined with one or more of the other parameters 160 in a particular configuration file 152. Thus, for example, format parameters 160*f* and subscription parameters 160*e* may be defined such that certain types of subscriptions must use a particular format. As another example, the format parameters 160*f* may be combined with the address parameters 160*c* and/or the transceiver parameters 160*a* such that devices with certain addresses, or devices that utilize a particular transceiver 138, are only able to use certain types of message formats. Still other combinations of parameters 160 may be implemented in a particular configuration file 152.

The allowable format parameters 160*f* may dictate what types of formats are to be used at a universal level, or they may dictate what types of formats are to be used at an individualized and/or contingent level. With respect to the former, the format data 160*f* may universally dictate, for example, that the patient support apparatus and/or thermal control unit data is all communicated with a particular format. Alternatively, the format parameters 160*f* may be individualized such that a first set of patient support apparatus data or thermal control unit data is communicated in a first format and a second set of patient support apparatus data or thermal control unit data is communicated in a second format. Still other variations in what messages are formatted in what manner are possible.

Similar to the other allowable parameters 160*a-e*, the format data 160*f* does not specify a particular format for any messages, but instead merely defines what types of formats are possible. That is, it is a list of permitted formats, not a command to implement a particular format. As will be discussed in more detail below, the default settings 162 may contain one or more formats that the gateway node 92, 92*a* is instructed, by default, to utilize when communicating with one or more off-board devices.

In addition to the allowable parameters 160*a-f*, configuration file 152 also contains a set of default settings 162 within the off-board settings 154 set of data (FIG. 7). The default settings 162 instruct gateway node 92, 92*a* how to process incoming messages received from off-board devices, as well as how to formulate outgoing messages to the off-board devices. The default settings 162 therefore may dictate what transceiver(s) 138 to use, what commands to follow, what addresses to receive messages from and/or to send messages to, what data to send to the off-board device(s), what subscriptions to implement, and/or what format the inbound and outbound messages have. Still other data may be contained within the default settings 162 that specify how gateway node 92, 92*a* is to act with respect to communications with off-board devices.

In some embodiments, one or more items of data contained within the default settings 162 may be changed in response to a command from an off-board device, such as, but not limited to server 120. Thus, the default settings are modifiable in some embodiments, provided the modifications are in accordance with the sets of allowable parameters 160*a-f*. If the modifications are not in accordance with the sets of allowable parameters 160*a-f*, the modifications cannot be made unless a new configuration file 152 is transferred to the patient support apparatus 20 or thermal control unit 174 to replace the existing configuration file 152, wherein the new configuration file 152 includes allowable parameters 160*a-f* that permit the modifications to the default settings.

In addition to the off-board settings 154, configuration file 152 also contains a set of onboard settings 156 (FIG. 7). Onboard settings 156 are similar to off-board settings 154 except that they apply to messages received from, and sent to, onboard network 146 or 248 rather any off-board devices. Thus, off-board settings 154 control the communications between gateway node 92, 92*a* and the off-board devices while onboard settings 156 control the communications between gateway node 92, 92*a* and the onboard structures (e.g. the nodes on network 146 or 248).

Onboard settings 156 include a set of allowable parameters 164*a-e* that are the same as the allowable parameters 160*a-e* of off-board settings 154. The only difference is that these parameters apply to the communications between node 92, 92*a* and the structures onboard patient support apparatus 20 or onboard thermal control unit 174. Thus, the allowable transceiver parameters 164*a* specifies what onboard transceivers 140*a-d* can be used for the onboard communications between node 92, 92*a* and network 146, 248 (or other structures onboard patient support apparatus 20 or thermal control unit 174). The allowable command parameters 164*b* specify what commands gateway node 92, 92*a* may send to onboard network 146 or 248, as well as what commands gateway node 92, 92*a* is able to receive from onboard network 146 or 248. The allowable address parameters 164*c* specify what addresses, or other routing information, can be used for the communications between gateway node 92, 92*a* and network 146 or 248. The retrievable data parameters 164*d* specify what data may be retrieved from the various nodes on network 146 or 248 by gateway 92, 92*a*. The allowable subscription parameters 164*e* specify what subscriptions gateway node 92, 92*a* is able to establish with each of the nodes of the onboard network 146 or 248. And the allowable format parameters 146*f* specify what formats are allowed for messages between gateway node 92, 92*a* and the nodes of onboard network 146 or 248.

Onboard settings 156 permit gateway node 92. 92*a* to easily adjust to modifications that are made to one or more of the structures onboard patient support apparatus 20 or thermal control unit 174. For example, if a new node is added to onboard network 146 or 248, configuration file 152 includes an allowable address for that new node such that communication with that new node may take place without having to stop the operation of controller 136 and load new executable code for controller 136. Instead, a command may be received from either onboard or off-board patient support apparatus 20 or thermal control unit 174 instructing gateway node 92 or 92*a* of the new node and its new address information, thereby enabling gateway node 92 or 92*a* to communicate with the node.

Similarly, if an existing node is modified so that it can perform a new function, gateway node 92, 92*a* may be able to command the performance of that new function or gather data regarding that new function without having to replace the executable code 150 for gateway controller 136. This may be accomplished in at least two different ways. In the first way, the currently utilized configuration file 152 may already contain the commands for commanding the new function within acceptable command parameters 164*b* and it may already specify in the allowable retrievable data parameters 164*d* that data regarding the new function is retrievable by gateway node 92, 92*a*. In this case, a simple command to the gateway node 92, 92*a* to implement the new function or to read data regarding the new function can be utilized. In the second way, a new configuration file 152 may be transferred to the medical device (e.g. patient support apparatus 20 or thermal control unit 174) that includes the new function and/or the newly retrievable data within its acceptable parameters 164*b*, 164*d*.

As with off-board data 154, onboard data 156 likewise includes one or more default settings 166. The default settings 166 instruct gateway node 92, 92*a* how to process incoming messages received from onboard network 146 or 248, as well as how to formulate messages that are delivered to the onboard network 146 or 248. The default settings 166 therefore may dictate what transceiver(s) 140 to use, what commands to follow, what addresses to receive messages from and/or to send messages to, what data to send to the network 146 or 248, what subscriptions to implement, and/or what format the inbound and outbound messages have (with respect to onboard network 146 or 248). Still other data may be contained within the default settings 166 that specifies how gateway node 92, 92*a* is to act with respect to the internal communications onboard patient support apparatus 20 or thermal control unit 174.

In some embodiments, one or more items of data contained within the default settings 166 may be changed in response to a command from an off-board device or an onboard node. Thus, the default settings 166 are modifiable in some embodiments, provided the modifications are in accordance with the sets of allowable parameters 164*a-f*. If the modifications are not in accordance with the sets of allowable parameters 164*a-f*, the modifications cannot be made unless a new configuration file 152 is transferred to the medical device to replace the existing configuration file 152, wherein the new configuration file 152 includes allowable parameters 164*a-f* that permit the modifications to the default settings 166.

It will be understood that the sets of allowable parameters 160 and 164 of configuration file 152 shown in FIG. 7 can be modified from what is shown therein. That is, configuration file 152 may include either additional allowable parameters 160 and/or 164 or fewer allowable parameters 160 and/or 164. Still further, different types of allowable parameters 160 and/or 164 may be substituted for one or more of the allowable parameters 160 and/or 164 shown in FIG. 7. In some modified embodiments, one or more of the parameters 160 and/or 164 shown in FIG. 7 are replace by instructions contained within executable code 150 such that those one or more parameters are no longer dynamically modifiable without performing a software update on patient support apparatus 20 and/or thermal control unit 174, which typically requires re-booting those devices and/or power cycling those devices.

It will also be understood that, in at least one embodiment, configuration file 152 includes data defining how gateway node 92, 92*a* is to implement each of the functions associated with each of the allowed parameters 160*a-f* and 164*a-f*. Thus, in addition to defining what actions or other parameters are permitted, configuration file 152 may include data specifying how gateway controller 136 is to, for example, format a message according to the acceptable format parameters 160*f* or 164*f*, or how react to the commands contained within the allowable command parameters 160*b* or 164*f*, and so on.

In some embodiments, configuration file 152 is written in the standard eXtensible Markup Language (XML) format. In other embodiments, configuration file 152 may be written in other formats. Regardless of the specific format, configuration file 152 is read and/or replaced in accordance with instructions contained within executable code 150, thereby allowing controller 136 to switch to new configuration files without having to be rebooted and/or power cycled.

It will be understood that all of the different allowable parameters 160*a-f* and 164*a-f* may be intermixed in a variety of different manners. By doing so, gateway node 92, 92*a* may be configured so that, as one example, it is only able to send messages to an off-board device if that off-board device communicates with an acceptable transceiver 138*a-d* according to transceiver parameters 160*a*, if the command to send such data is an acceptable command according to the command parameters 160*b*, if that off-board device has an acceptable address according to parameters 160*a*, if the message contains data that is acceptable according to retrievable data 160*d*, if the message is part of an acceptable subscription, and/or if the message is sent in a particular format. Similar intermixing of parameters 164 with each other, as well as with parameters 160, may be implemented.

It will be understood that, although several different types of data have been specifically mentioned as being communicated between gateway node 92, 92*a* and one or more off-board devices, a wide variety of data not explicitly mentioned herein may be transmitted by gateway node 92, 92*a* subject to the restraints and permissions of configuration file 152. This additional data includes, but is not limited to, any data from any of the sensors onboard patient support apparatus 20 or thermal control unit 174. In different embodiments, patient support apparatus 20 may be modified to include any one or more sensors for detecting the characteristics identified in the first table of patent references below, and may transmit data from any one or more of these sensors to an off-board device via gateway node 92 and subject to the constraints and permissions of configuration file 152. All of the patent references in the table listed below are hereby incorporated herein by reference in their entirety.

| U.S. patent/ U.S. patent application Ser. No. | Filing Date | Title | Characteristic Detected |
|---|---|---|---|
| 5,276,432 | Jan. 15, 1992 | Patient Exit Detection Mechanism for Hospital Bed | Patient's location (center of gravity) |
| 7,699,784 | Jul. 5, 2007 | System for Detecting and Monitoring Vital Signs | Patient's heart rate, breathing rate, and other vital signs |
| 9,320,444 | Mar. 14, 2014 | Patient Support Apparatus with Patient Information Sensors | Patient sleep quantity, quality, and other sleep parameters; patient weight |
| 61/449,182 | Mar. 4, 2011 | Sensing System for Patient Supports | Patient interface pressures, vital signs, |
| 14/692,871 | Apr. 22, 2015 | Person Support Apparatus with Position Monitoring | Patient movement |
| 14/873,734 | Oct. 2, 2015 | Person Support Apparatus with Motion Monitoring | Patient and object weights, movement, and position |
| 14/928,513 | Oct. 30, 2015 | Person Support Apparatus with Patient Mobility Monitoring | A patient's activity, time out of bed, number of steps, and other activity data |
| 14/578,630 | Dec. 22, 2014 | Video Monitoring System | Patient turns, bed sore assessment scores, eating and sleeping, exit detection system status, etc. |
| 15/346,779 | Nov. 9, 2016 | Person Support Apparatus with Acceleration Detection | Patient vital signs, position, movement |
| 15/809,351 | Nov. 10, 2017 | Patient Support Apparatuses with Mobility Assessment | Patient mobility score and/or assessments |
| 15/709,586 | Sep. 20, 2017 | Systems and Methods for Determining the Usability of Person Support Apparatuses | Cleanliness and/or usability status of a patient support apparatus |

Similarly, in different embodiments, thermal control unit 174 may be modified to include any one or more sensors for detecting the characteristics identified in the second table of patent references below, and may transmit data from any one or more of these sensors to an off-board device via gateway node 92*a* and subject to the constraints and permissions of configuration file 152. All of the patent references in the table listed below are hereby incorporated herein by reference in their entirety

| Patent/ U.S. patent application Ser. No. | Filing Date | Title | Characteristic Detected |
|---|---|---|---|
| 15/820,558 | Nov. 22, 2017 | Thermal System | Patient shivering |
| 15/729,173 | Oct. 10, 2017 | Thermal Control System | Quality of circulating fluid |
| 15/616,574 | Jun. 7, 2017 | Thermal Control System | Thermal data from previous therapy |
| 15/675,061 | Aug. 11, 2017 | Thermal Therapy Devices | Characteristics of secondary fluids in pads 178 |
| 16/218,883 | Dec. 13, 2018 | Thermal System with Overshoot Reduction | Fan speed, current PID coefficients, reservoir temperature, current flow path, |
| 16/169,271 | Aug.24, 2018 | Thermal System with Medication Interaction | Administered medication; temperature reaction to medication |
| 16/222,004 | Dec. 17, 2018 | Thermal System with Graphical User Interface | Heat transfer for each pad 178 |
| 16/957,809 | Jun. 25, 2020 | Thermal System with Patient Sensors | Patient size, bioimpedance, BMI, $ETCO_2$ readings |
| 16/912,244 | Jun. 25, 2020 | Thermal System with User Interface Customization | Patient electrolyte levels, customized settings, therapy profiles |
| 16/912,256 | Jun. 25, 2020 | Thermal System with Improved User Interface | Statistical data from multiple thermal therapy sessions |

It will also be understood that, in some embodiments, the messages that travel on local onboard network 146 or 248 do not include any address information for being transmitted off-board patient support apparatus 20 or thermal control unit 174. In such embodiments, gateway node 92, 92*a* includes this address information as part of its configuration file. Thus, the individual nodes on the onboard network 146 or 248 do not need to know anything about whether the data they generate will get transferred off of the medical device or not. Indeed, in some embodiments, the data they generate may be both transferred to one or more local recipients onboard the medical device and also transmitted off of the medical device via gateway node 92 or 92*a*.

For example, in some embodiments, main control node 52 of patient support apparatus 20 processes the outputs of load cells 80 to determine the patient's weight and transmits a message on local network 146 that indicates the patient's current weight. This message is received by all of the nodes on network 146. Some of the nodes may not do anything with the message, while other nodes may react to it. For example, display node 56 may be programmed to react to the message by reading it and displaying the patient weight reading on display 90*a* or 90*b*. Gateway node 92 may also be programmed to react to the patient weight reading message by transmitting the patient weight reading to patient support apparatus server 120 using WiFi transceiver 138*c*. The weight reading message from main control node 52 does not need to specify that gateway node 92 transmits the patient weight reading off the patient support apparatus 20, nor does it need to specify the address that gateway node 92 uses to transmit the patient weight reading message to. Instead, this address information is stored in configuration file 152 of gateway node 92 (e.g. included within address parameters 160*c*). Updates and/or changes of the gateway node 92 can therefore cause patient support apparatus 20 to change what information is transmitted to off-board devices without requiring any changes to any of the executable code of patient support apparatus 20.

Similar types of changes can be made to gateway node 92*a* of thermal control unit 174. For example, in some embodiments, I/O control node 238 sends a message on local onboard network 248 that indicates the patient's current temperature reading (as measured by one or more temperature probes 252). This message may be read by main control node 224 and displayed on display 198. This same message may also be read by gateway node 92*a* and, depending upon the configuration file 152 currently installed in gateway node 92*a*, may prompt gateway node 92*a* to send the current patient temperature reading to one or more off-board servers (e.g. server 120 and/or 130). The patient temperature reading message from I/O node 238 does not need to specify that gateway node 92*a* transmits the patient temperature reading off the thermal control unit 172, nor does it need to specify the address that gateway node 92*a* uses to transmit the patient temperature reading message to. Instead, this address information is stored in configuration file 152 of gateway node 92*a* (e.g. included within address parameters 160*c*). Updates and/or changes of the gateway node 92*a* can therefore cause thermal control unit 174 to change what information is transmitted to off-board devices without requiring any changes to any of the executable code of thermal control unit 174.

In both of the foregoing examples, the transmission of the data off the medical device (e.g. patient weight for patient support apparatus 20 and patient temperature for thermal control unit 174) by gateway node 92 or 92*a* may be part of the default programming of the configuration file 152 used with these nodes 92 or 92*a*, or this transmission may be turned on/off through the use of a new configuration file 152. That is, in some embodiments, a new configuration file 152 may be transferred to gateway node 92 or 92*a* that either turns on, or turns off, the transmission or the patient weight or temperature to one or more remote devices. Similar types of changes can be made for all of the other sensor readings and/or other parameters that are transmitted onboard the local network 146 or 248.

Figure 8:
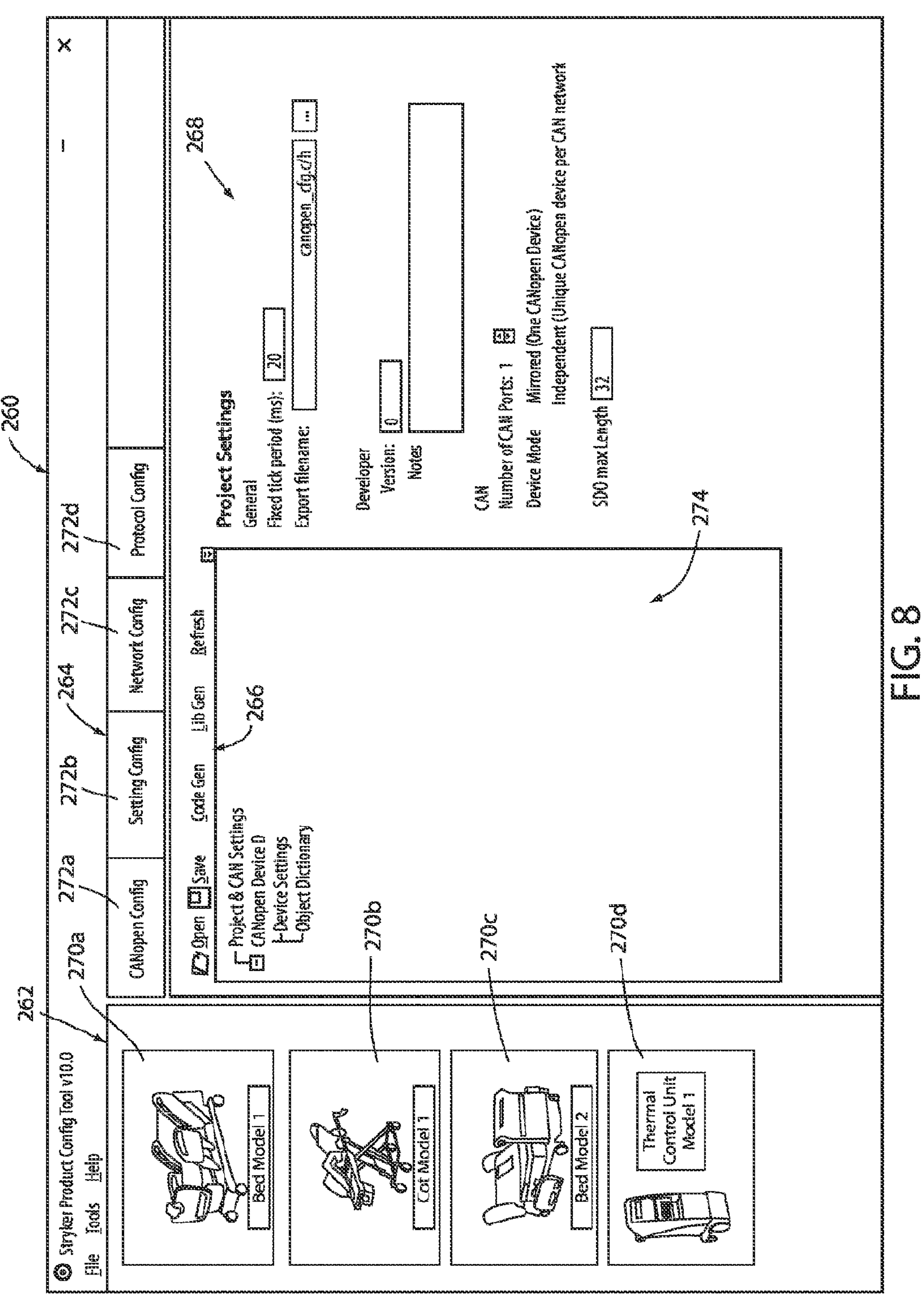
FIG. 8 is a first illustrative screenshot of a configuration tool that may be used to configure the gateway node.

FIG. 8 illustrates an illustrative screen shot from a gateway configuration tool that may be used to more efficiently create and edit configuration file 152. The gateway configuration tool may be executed on a conventional laptop computer, on a tablet computer, and/or on any other general programmable device. The gateway configuration tool is used by an authorized person when he or she wishes to make changes to a configuration file 152, create a new configuration file 152, and/or, in some cases, transfer a configuration file 152 to a particular medical device (e.g. patient support apparatus 20 or thermal control unit 174).

FIG. 8 illustrates an example of an initial screen or home screen that may be displayed by the gateway configuration tool. Screen 260 includes a medical device selection column 262, a plurality of configuration options 264*a-d*, an action tool bar 266, and an editing window 268. The user uses device selection column 262 to select which type of medical device he or she would like to create a configuration file 152 for. In the example show in FIG. 8, there are four medical device options 270*a-d*. A first option 270*a* corresponds to a first model of a patient support apparatus 20, such as a bed. A second option 270*b* corresponds to a first model of a different type of patient support apparatus 20, such as a cot. A third option 270*c* corresponds to a second model of a bed 20. And a fourth option corresponds to thermal control unit 174. It will, of course, be understood that additional medical device options may be present in column 262, and/or that any of the options 270*a-d* shown therein may be modified and/or replaced in other embodiments of the gateway configuration tool.

After a user has selected one of options 270*a-d*, gateway configuration tool is generate an initial configuration file for that selected medical device that can then be edited by the user. The initial configuration file may be generated based on an initially designed configuration for the corresponding gateway node of that particular medical device. This initial design may be designed by the manufacturer of the selected medical device based on their assumptions regarding the desired functionality of the gateway node. Alternatively, or additionally, the gateway configuration tool may be configured to allow a user to generate an initial configuration file 152 from scratch, or from one or more pieces of information that are stored in the configuration tool regarding that particular device (e.g. a CAN object dictionary—if the device uses a CAN network, and/or any one or more initial settings 160 or 164 (see FIG. 7)) of the configuration file.

After the user has selected a particular medical device from column 262, he or she can select an action from tool bar 266 and/or select a group of parameters to configure on the medical device. The groups of parameters includes a first set 272*a* of CANOpen configuration parameters, a second set 272*b* of setting configuration parameters, a third set 272*c* of network configuration parameters, and a fourth set 272*d* of protocol configuration parameters. Other groupings and/or sets of parameters may be used with the gateway configuration tool. In one embodiment, first set 272*a* includes command parameters 160*b* and format parameters 160*f*; second set 272*b* includes retrievable data parameters 160*d* and subscription parameters 160*e*; third set 272*c* includes transceiver parameters 160*a*; and fourth set 272*d* includes address parameters 160*c*. It will, of course, be understood that other groupings and/or correlations between sets 272 and parameters 160 may be utilized. Default parameters 162 may be included within each of the sets 272*a-d*.

After the user has selected a particular set 272 of parameters, the gateway configuration tool is configured to display the selected parameters in a display area 274. Thus, for example, if a user selects the CANOpen set of parameters 272*a*, the gateway configuration tool may be configured to display a screen like screen 290 of FIG. 9. Screen 290 illustrates an example of a various CANOpen parameters shown in display area 274. More specifically, screen 290 shows a portion of a CANOpen object dictionary for messages traveling on the onboard network 146 of the patient support apparatus 20 (specifically, the first model corresponding to option 270*a*). If the uses selects a particular entry 282 in the object dictionary, the gateway configuration tool is configured to display additional information about that particular object in the editing area 268. For some entries, such as entry 280*a*, the gateway configuration tool is configured to display additional sub-entries in the display area 274 when a user selects that particular entry. Thus, if the user presses on entry 280*a*, the configuration tool may be configured to display additional entries 280*b*, 280*c*, 280*d*, and 280*e*.

The user is then able to select any of the entries 280 or subentries 280. In the particular example shown in FIG. 9, the user has selected sub-entry **280*b* and the configuration tool is displaying additional information about that particular sub-entry 280 in editing area 268. Editing area 268 is configured to allow the user to change various values of the sub-entry 280, such as, but not limited to, its description, its type, its length, its access level, its value, whether it is indirect or direct, a default flag, and/or a variable name for the entry. The particular set of values shown in editing area 268 may be increased, decreased, and/or substituted with one or more other types of values, depending upon the particular entry or sub-entry 280 that is selected and/or the particular medical device whose configuration file 152** is being edited.

Although not shown in the accompanying drawings, when the user selects any of the other sets of parameters 272, the gateway configuration tool is configured to display additional information about those parameters in display area 274 and to allow the user to edit those parameters in editing window 268. After the user has made the desired edits to all of the desired settings, the user can generate the configuration file 152 by pressing on the "Lib Gen" action 284 of tool bar 266. Once action 284 is activated, the user has the option of saving the configuration file 152 somewhere on the computer that is executing the gateway configuration tool. From there, the configuration file 152 can be transferred to the desired medical device (e.g. patient support apparatus 20 and/or thermal control unit 174) and utilized by the corresponding gateway node 90, **90*a***.

Three examples of the types of command messages that a medical device can be configured to carry out via an appropriate configuration file 152 are shown in the table below. These three examples are shown in the second through fourth rows of the table below. In the first example, configuration file 152 is constructed so that the gateway node 92, **92*a* can receive a command (command index 1) that sets the gateway node 92, 92*a* into its access point mode. In the second example, configuration file 152 may be constructed so that an electric brake on patient support apparatus 20 can be remotely controlled by a device positioned off-board the patient support apparatus 20. In the third example, configuration file 152 may be constructed to that the status of the electric brake may be transmitted to a device positioned off-board the patient support apparatus 20. The three examples shown in the table below are not meant to be exhaustive, but instead are merely illustrative examples of the types of parameters that may be set using the configuration file 152. The information shown in the table below is information that may all be entered into a configuration file 152** using the gateway configuration tool.

| Command Index | Client Side ID | Server Side ID | Type | Client Side Comm | Server Side Comm | Direction | Periodicity | Description |
|---|---|---|---|---|---|---|---|---|
| 1 | 0x00F | Gateway-Access Point Mode | Boolean | CAN | JSON | Server2Client | Set | Sets the gateway node 92, 92a into access point mode |
| 24 | 0x774 | E-Brake Feature-Enable | Boolean | CAN | JSON | Server2Client | Set | Sets a patient support apparatus feature, in this case the electric brake |
| 75 | 0x123 | Brake-ON | Boolean | CAN | JSON | Client2Server | Subscribe | Subscribe to the brake on/off feature and send info as needed |

In the above table, the "client side ID" refers to the identification used by the medical device (e.g. patient support apparatus 20 and/or thermal control unit 174) for a particular command message. The "server side ID" refers to the identification used by the off-board device (e.g. server 120, 130, etc.) for a particular command message. The "client side comm" refers to the communication protocol used by the medical device, and the "server side comm" refers to the communication protocol used by the off-board device. As was mentioned previously, in some embodiments, the "client side comm" and/or the "server side comm" may refer to other protocols besides CAN, such as, but not limited to, USB, Ethernet, CANOpen, LIN, etc. The "direction" column refers to the direction in which the data flows for the corresponding command message (e.g. from medical device to off-board device, or vice versa). The periodicity refers to the frequency and/or timing of the command message. In addition to the "set" and "subscribe" options shown above, the periodicity may also include other options, such as, but not limited to, a "get" command message in which data is retrieved on a one-time basis from the recipient of the command.

It will, of course, be understood that the three examples shown in the above table are merely a small example of the types of commands messages that may be utilized with the gateway node 92 of patient support apparatus 20 and/or the gateway node **92*a* of thermal control unit 174. In some embodiments, thermal control unit 174 may include an object dictionary that includes all of, or a subset of, the messages listed in the table below, and one or more commands pertaining to any one or more of these messages may be carried out by gateway node 92*a* using the currently installed configuration file 152** (which may be constructed using the gateway configuration tool).

| Message | Periodicity | Direction | Description |
|---|---|---|---|
| Date and Time | Every data point | Client2Server | All, or a subset of, the data includes a time and date stamp |
| Session ID | On change | Client2Server | An ID used to identify a particular thermal therapy session |
| Supplied Water Temp | Every minute | Client2Server | Water Temp measured by sensor 222 |
| Returned Water Temp | Every minute | Client2Server | Water temp sensed by sensor in inlet manifold 226 |
| Patient Temp | Every minute | Client2Server | Patient temp sensed by probe(s) 252 |
| Port Flows | Every minute | Client2Server | Water flow through outlet ports 186 and/or inlet ports 188 |
| Heating/Cooling Trend (Power) | Every minute | Client2Server | Power level delivered to heat exchanger 206 |
| System Flow | Every minute | Client2Server | Total flow through ports 186 and/or ports 188 |
| Final Target Temp | Every minute and on change | Client2Server | Target temp for patient at the end of thermal therapy session |
| Current Target Temp | Every minute and on change | Client2Server | Target temp for patient at the current moment in the thermal therapy session |
| Events | On change | Client2Server | Various events (e.g. mode change, therapy paused, etc.) |
| Alarms | On change | Client2Server | Various alarms (e.g. shivering detected, flow drops, temp outside of range, etc.) |
| Service Error Code | On change | Client2Server | Error codes requiring service |
| Service Error Value | On change | Client2Server | Values associated with the error codes |
| Mode Changed | On change | Client2Server | Changes to thermal therapy mode (e.g. manual, automatic) |
| Primary Probe Changed | On change | Client2Server | Change of which probe 252 is being used in automatic mode |
| Therapy Rate Changed | On change | Client2Server | Change in the default rate at which patient is being cooled/warmed |
| Custom Rate Changed | On change | Client2Server | Change in the customized rate at which patient is being cooled/warmed |
| Ports Selected Changed | On change | Client2Server | Change in the ports 190 and/or ports 186 |
| Service Log Cleared | On change | Client2Server | Clearing of service log maintained in memory of thermal control unit (TCU) 174 |
| Disinfection Date | On change | Client2Server | Date when TCU 174 is disinfected |
| On Target Status | On change | Client2Server | Whether heating/cooling of patient is proceeding at a rate to meet target temperature |
| Software Version | Boot up | Client2Server | Software versions of software modules on TCU 174 |
| Serial Number | Boot up | Client2Server | Serial number of TCU 174 |
| Model Number | Boot up | Client2Server | Model number of TCU 174 |
| Safety Water Temps | Every min | Client2Server | Water temperature measured by safety temp sensors (not shown) |
| Fan Speeds | Every min | Client2Server | Speed of fan(s) in heat exchanger 206 |
| Control Box Temp | Every min | Client2Server | Temperature of control box in TCU 174 |
| Pump Speed | Every min | Client2Server | Speed of pump 200 |
| Refrigerant Temp | Every min | Client2Server | Temperature of refrigerant in heat exchanger 206 |
| Battery Health | When checked | Client2Server | Health parameters of battery (not shown) used with TCU 174 |
| Alarm Name/ID | On need | Server2Client | Name and ID of alarms issued by TCU 174 |
| Priority | On need | Server2Client | Priority level associated with a particular alarm |
| Audible Alarm enabled | On need | Server2Client | Command to change whether an alarm is issued audibly or not |
| Reminder Period | On need | Server2Client | Command to set reminder period for addressing an unacknowledged alarm |
| Alarm Tone | On need | Server2Client | Tone of a particular audible alarm |
| Profile name | On need | Server2Client | A name for a thermal therapy profile |
| Induction Target | On need | Server2Client | A target temperature for cooling a patient to a hypothermic state |
| Induction Therapy Rate | On need | Server2Client | Rate of cooling for inducing hypothermia |
| Notification for Target Achievement | On need | Server2Client | Command to issue a notification when target temperature is reached |
| Maintenance Duration | On need | Server2Client | Duration at which patient is kept at hypothermic temperature |
| Notification for Maintenance Completion | On need | Server2Client | Command to issue a notification when maintenance duration has been completed |
| Re-warming target | On need | Server2Client | Target temperature for re-warming the patient |
| Re-warming rate | On need | Server2Client | Rate at which patient is to be re-warmed |
| Notification for re-warming achievement | On need | Server2Client | Command to issue a notification when the maintenance duration has been completed |
| Target Temp | On need | Server2Client | Command to issue a notification when the patient target temp is changed |
| Therapy Rate | On need | Server2Client | Command to issue a notification when the cooling/heating rate is changed |
| Alarm Acknowledgement | On need | Server2Client | Command to issue a notification when an alarm is acknowledged |
| Mode Selection | On need | Server2Client | Command to issue a notification when the mode is changed |

It will be understood that the table immediately above is merely a representative sampling of the types of messages onboard thermal control unit 174 that gateway node 92*a* may be configured to process via configuration file 152. In some embodiments, thermal control unit 174 may be initially manufactured with a configuration file 152 that only includes a subset of the messages shown in this table, but then be subsequently modified through a new configuration file 152 to process additional messages and/or to remove one or more of these messages from its processing ability. For example, a thermal control unit 174 might initially be sold with a configuration file 152 for gateway node 92*a* that did not allow any parameters of the thermal control unit 174 to be controlled remotely. At some point out thereafter, a new configuration file 152 may be added to thermal control unit 174 that includes, for example, any one or more of the "server2client" messages in the table above.

For example, the new configuration file might include the "re-warming target" message, which allows a remote device to send a command to the thermal control unit 174 that specifies a target temperature of the patient that thermal control unit 174 should seek to achieve when re-warming the patient. When the new configuration file 152 is installed on thermal control unit 174 with this new "re-warming target" message included therein, and gateway node 92*a* receives a "re-warming target" message from an authorized off-board device, it places a command on the local, onboard network 248 in response to this message that contains the target temperature in the received message. The command placed on the local onboard network 248 is the same command that is placed on network 248 by one of the onboard nodes 224, 238, and/or 244 when the corresponding command is issued locally. The result is therefore the same as if one of the onboard nodes 224, 238, and/or 244 has issued the "re-warming target" message and placed it on network 248. The modification of configuration file 152 can therefore allow remote devices to behave as if they were nodes on onboard network 248.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal control unit for controlling a patient's temperature during a thermal therapy session, the thermal control unit comprising:

a circulation channel coupled to a fluid inlet and a fluid outlet;

a pump for circulating fluid through the circulation channel from the fluid inlet to the fluid outlet;

a heat exchanger adapted to add or remove heat from the fluid circulating in the circulation channel;

a plurality of nodes adapted to communicate with each other over a local network onboard the thermal control unit using a first communications protocol;

a controller adapted to control the heat exchanger in order to control the patient's temperature;

a gateway in communication with the local network and a remote device; the gateway including a gateway controller, a first transceiver, a second transceiver, and a memory containing an executable file and a configuration file; wherein the first transceiver is adapted to receive and transmit local messages on the local network that are in a first format, the second transceiver is adapted to receive and transmit messages on a remote network that are in a second format different from the first format, and the executable file contains instructions instructing the gateway controller to perform the following:

(a) read the configuration file to identify a set of messages on the local network;

(b) monitor the local network for individual messages contained within the set of messages;

(c) determine if any of the individual messages contain first subscribed content to which the remote device has a subscription, wherein the configuration file identifies the first subscribed content;

(d) format the first subscribed content into outbound messages according to the second format;

(e) forward the outbound messages to the remote network via the second transceiver;

(f) read a second configuration file to identify a second set of messages on the local network;

(g) monitor the local network for individual messages contained within the second set of messages;

(h) determine if any of the individual messages contain second subscribed content to which the remote device has a second subscription, wherein the second configuration file identifies the second subscribed content and the second subscribed content is different from the first subscribed content;

(i) format the second subscribed content into second outbound messages according to the second format; and (i) forward the second outbound messages to the remote network via the second transceiver.

2. The thermal control unit of claim 1 wherein the executable file further contains instructions instructing the gateway controller to read the configuration file to identify the second format and to read the configuration file to determine an address of the remote device.

3. The thermal control unit of claim 2 wherein the first format is a Controller Area Network (CAN) message format, the second format is a JavaScript Object Notation format, and the configuration file is an extensible Markup Language (XML) file.

4. The thermal control unit of claim 1 wherein the executable file further contains instructions instructing the gateway controller to perform the following:

(i) read the configuration file to identify a set of incoming messages from the remote network;

(ii) monitor the second transceiver for individual incoming messages contained within the set of incoming messages;

(iii) determine if any of the individual incoming messages contain node content which is to be forwarded to one or more nodes of the local network;

(iv) format the node content into local messages according to the first format; and (v) forward the local messages to the local network via the first transceiver.

5. The thermal control unit of claim 1 wherein the executable file further contains instructions instructing the gateway controller to perform the following without installing a different executable file:

(i) receive a new configuration file;

(ii) replace the configuration file with the new configuration file; and (iii) perform steps (a) through (e) using the new configuration file.

6. The thermal control unit of claim 5 wherein the executable file contains instructions instructing the gateway controller to perform at least one of the following: (1) receive the new configuration file via the second transceiver, or (2) receive the new configuration file via a third transceiver.

7. The thermal control unit of claim 1 further comprising a third transceiver in communication with the gateway controller and the remote network, the third transceiver adapted transmit and receive messages on the remote network that are in a third format, and wherein the executable file contains instructions instructing the gateway controller to perform the following:

(i) receive a new configuration file;
(ii) replace the configuration file with the new configuration file;
(iii) read the new configuration file to identify a new set of messages on the local network;
(iv) monitor the local network for individual messages contained within the new set of messages;
(v) determine if any of the individual messages contained within the new set of messages contain subscribed content to which the remote device has a subscription;
(vi) read the new configuration file to determine which of the second transceiver and third transceivers is a selected transceiver for communicating the subscribed content to the remote device;
(vii) format the subscribed content into outbound messages according to a corresponding format of the selected transceiver; and
(viii) forward the outbound messages to the remote network via the selected transceiver.

8. The thermal control unit of claim 1 wherein the set of messages on the local network includes a message containing a temperature of the fluid.

9. A thermal control unit for controlling a patient's temperature during a thermal therapy session, the thermal control unit comprising:

a circulation channel coupled to a fluid inlet and a fluid outlet;
a pump for circulating fluid through the circulation channel from the fluid inlet to the fluid outlet;
a heat exchanger adapted to add or remove heat from the fluid circulating in the circulation channel;
a plurality of nodes adapted to communicate with each other over a local network onboard the thermal control unit using a first communications protocol;
a controller adapted to control the heat exchanger in order to control the patient's temperature;
a gateway in communication with the local network and a remote device; the gateway including a gateway controller, a first transceiver, a second transceiver, and a memory containing an executable file and a configuration file; wherein the first transceiver is adapted to receive and transmit local messages on the local network that are in a first format, the second transceiver is adapted to receive and transmit messages on a remote network that are in a second format different from the first format, and the executable file contains instructions instructing the gateway controller to perform the following:
(a) read the configuration file to identify a first set of messages to be received from the remote network;
(b) monitor the second transceiver for individual messages contained within the first set of messages, the first set of messages including a first message requesting a reading of a current temperature of the fluid but not including a second message requesting a reading of a current flow rate of the fluid through the circulation channel;
(c) read the configuration file to determine if any of the individual messages contain node content to be forwarded to an individual node of the plurality of nodes on the local network;
(d) format the node content into onboard messages according to the first format, wherein the configuration file identifies the first format;
(e) forward the onboard messages to the local network via the first transceiver;
(f) receive a new configuration file and, without rebooting the gateway controller, perform the following:
(1) read the new configuration file to identify a second set of messages to be received from the remote network and forwarded to the local network, the second set of messages including the second message; and
(2) forward content from the second set of messages to the local network.

10. The thermal control unit of claim 9 wherein the executable file further contains instructions instructing the gateway controller to perform the following:

(i) read the configuration file to identify a set of local messages on the local network;
(ii) monitor the local network for individual local messages contained within the set of local messages;
(iii) determine if any of the individual local messages contain subscribed content to which the remote device has a subscription;
(iv) format the subscribed content into outbound messages according to the second format; and
(v) forward the outbound messages to the remote network via the second transceiver.

11. The thermal control unit of claim 9 wherein the configuration file includes at least two of the following: a Service Set Identifier (SSID) for the remote network, a password for accessing the remote network, a Transmission Control Protocol (TCP) port number for communicating with the remote device, an IP address of the remote device, a definition of the first format, or a definition of the second format.

12. A thermal control unit for controlling a patient's temperature during a thermal therapy session, the thermal control unit comprising:

a circulation channel coupled to a fluid inlet and a fluid outlet;
a pump for circulating fluid through the circulation channel from the fluid inlet to the fluid outlet;
a heat exchanger adapted to add or remove heat from the fluid circulating in the circulation channel;
a plurality of nodes adapted to communicate with each other over a local network onboard the thermal control unit using a first communications protocol;
a controller adapted to control the heat exchanger in order to control the patient's temperature;
a gateway in communication with the local network and a remote device; the gateway including a gateway controller, a first transceiver, a second transceiver, and a memory containing an executable file and a configuration file; wherein the first transceiver is adapted to receive and transmit local messages on the local network that are in a first format, the second transceiver is adapted to receive and transmit messages on a remote network that are in a second format different from the first format, and the executable file contains instructions instructing the gateway controller to perform the following:

(a) read the configuration file to identify a first set of messages to be received from the remote network and forwarded to the local network;

(b) forward content from the first set of messages to the local network in the first format, the first format being identified by the configuration file;

(c) receive a new configuration file and, without rebooting the gateway controller, perform the following:

(i) read the new configuration file to identify a second set of messages to be received from the remote network and forwarded to the local network, the second set of messages including a new message not contained within the first set of messages, and wherein the new message instructs a particular node on the thermal control unit to activate a sensor in communication with the particular node and to report a reading from the sensor to the local network; and (ii) forward content from the second set of messages to the local network.

13. The thermal control unit of claim 12 wherein the executable file further contains instructions instructing the gateway controller to perform the following:

(i) read the new configuration file to identify a set of local messages on the local network;

(ii) monitor the local network for individual local messages contained within the set of local messages;

(iii) determine if any of the individual local messages contain subscribed content to which the remote device has a subscription;

(iv) format the subscribed content into outbound messages according to the second format; and (v) forward the outbound messages to the remote network via the second transceiver.

14. The thermal control unit of claim 12 wherein the configuration file includes at least two of the following: a Service Set Identifier (SSID) for the remote network, a password for accessing the remote network, a Transmission Control Protocol (TCP) port number for communicating with the remote device, an IP address of the remote device, a definition of the first format, or a definition of the second format.

15. The thermal control unit of claim 12 wherein the executable file further contains instructions instructing the gateway controller to read the new configuration file to identify a message ID associated with the second set of messages, and to attach the message ID to the content forwarded from the second set of messages to the local network.

16. The thermal control unit of claim 12 wherein the first set of messages from the remote network includes a first message requesting a reading of a current temperature of the fluid but does not include a second message requesting a reading of a current flow rate of the fluid through the circulation channel, and the second set of messages includes the second message.

* * * * *